(12) United States Patent
Sasaki et al.

(10) Patent No.: US 6,323,163 B1
(45) Date of Patent: Nov. 27, 2001

(54) FLUOROCOMPOUND, LUBRICANT, SURFACE MODIFIER, LUBRICATING FILM, MAGNETIC RECORDING MEDIUM, AND MAGNETIC RECORDING DEVICE

(75) Inventors: Hiroshi Sasaki; Mitsuyoshi Shouji, both of Ibaraki-ken; Takayuki Nakakawaji, Kitaibaraki; Tomoe Takamura; Mina Ishida, both of Hitachi; Yutaka Ito, Takahagi; Hiroyuki Matsumoto, Chigasaki, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/284,610

(22) PCT Filed: Oct. 9, 1997

(86) PCT No.: PCT/JP97/03190

§ 371 Date: Jun. 17, 1999

§ 102(e) Date: Jun. 17, 1999

(87) PCT Pub. No.: WO98/17617

PCT Pub. Date: Apr. 30, 1998

(30) Foreign Application Priority Data

Oct. 17, 1996 (JP) .................................................. 8/274899

(51) Int. Cl.$^7$ ..................... C10L 105/54; C10M 105/68; C10M 105/70; C07C 43/12; C07D 273/01

(52) U.S. Cl. .......................... 508/307; 508/308; 540/467; 549/351; 549/352; 549/353

(58) Field of Search ..................................... 508/307, 308; 540/467; 549/351, 352, 353

(56) References Cited

U.S. PATENT DOCUMENTS 4,523,994 * 6/1985 Shono et al. .
4,554,362 * 11/1985 Shono et al. .
4,721,795 * 1/1988 Caporiccio et al. .
4,808,472 * 2/1989 Caporiccio et al. .
5,663,127 * 9/1997 Flynn et al. .
6,025,310 * 2/2000 Nishiguchi et al. .

FOREIGN PATENT DOCUMENTS

| 61-004727 | 1/1986 | (JP) . |
| 5-258287 | 10/1993 | (JP) . |
| 7-216375 | 8/1995 | (JP) . |
| 8-036741 | 2/1996 | (JP) . |
| 8-036742 | 2/1996 | (JP) . |
| 8-231455 | 9/1996 | (JP) . |
| 8-259482 | 10/1996 | (JP) . |

OTHER PUBLICATIONS

"Journal of Polymer Science", W.M. Feigenbaum & R.H. Michel Part–A–1, vol. 9, pp. 817–820, 1970.

"Journal of the Organic Chemistry", S.A.G. Hogberg & D.J. Cram, vol. 40, pp. 151–152, 1975.

"Journal of the American Chemical Society", R. Ungaro, B. El Haj & J. Smid, 98:17, pp. 5198–5202, Aug. 18,1976.

* cited by examiner

Primary Examiner—Jerry D. Johnson
(74) Attorney, Agent, or Firm—Antonelli, Terry, Stout & Kraus, LLP

(57) ABSTRACT

The present invention is a fluorine-containing compound having i) a perfluoropolyoxyalkyl or -alkylene chain having an average molecular weight of 800 or more and ii) a cyclic or non-cyclic polyether atomic group. Its use as a low-scattering lubricant or surface modifier (water repellent) brings about an improvement in sliding durability of magnetic recording media.

29 Claims, 7 Drawing Sheets

IR SPECTRUM OF COMPOUND 1

IR SPECTRUM OF COMPOUND 12

¹H-NMR SPECTRUM OF COMPOUND 16

IR SPECTRUM OF COMPOUND 17

IR SPECTRUM OF COMPOUND 18

IR SPECTRUM OF COMPOUND 27

IR SPECTRUM OF COMPOUND 35

SCHEMATIC DIAGRAM OF CROSS-SECTION OF
MAGNETIC RECORDING MEDIUM OF THE PRESENT INVENTION

CROSS-SECTIONAL VIEW OF MAGNETIC RECORDING DEVICE OF THE PRESENT INVENTION

FLUOROCOMPOUND, LUBRICANT, SURFACE MODIFIER, LUBRICATING FILM, MAGNETIC RECORDING MEDIUM, AND MAGNETIC RECORDING DEVICE

TECHNICAL FIELD

This invention relates to a fluorine-containing compound especially effective for improving sliding durability of magnetic recording media, a low-scattering lubricant or surface modifier containing the compound, a lubricating film formed using the same, and a magnetic recording medium having such a lubricating film.

BACKGROUND ART

In recent years, the distance between a head and a disk has shown a tendency to become smaller because of the necessity to make magnetic disk devices have a higher recording density. The speed of revolution of a disk has also shown a tendency to increase because of the necessity to perform read/write at a high speed. This causes the head and the disk to come into contact more frequently, and moreover come into contact at a higher speed than ever. Hence, it is foreseen that disks will slide as the operating conditions become more severe than ever. Accordingly, in order to prevent magnetic layers from wearing away because of such a sliding movement, lubricants used in the outermost layers of magnetic disks have been improved in variety.

For example, a fluorine-containing compound such as a compound having piperonyl groups at both terminals of a perfluorooxyalkylene chain (Japanese Patent Application Laid-open No. 61-4727) is proposed as a lubricant which may be coated on the surfaces of magnetic disks to improve the lubricity of their surfaces to reasonably restrain the wear of magnetic layers.

However, such a lubricant may be gradually scattered by the sliding of a head. This is considered to be due to the lubricant being physically scraped off by sliding movement or due to volatilization caused by heat energy produced by sliding movement. Accordingly, low-scattering lubricants are desired since the use of a disk for a long time may cause the lubricant layer on the disk surface to become thin or, in some cases, may cause its underlying layer to become laid bare in parts.

In particular, in recent years, as the distance between the head and the disk is made smaller in order to make magnetic disk devices have a higher recording density, the head and the disk come into contact very frequently. Thus, the lubricants must be durable to cope with severe slide conditions. In particular, recently with heads and head sliders being made small-sized, the head tends to have a lower rigidity than ever. Hence, such a head has caused a problem of being broken because of its great stickiness to the disk, when the disk is started to turn.

Accordingly, a first object of the present invention is to provide a fluorine-containing compound having a good sliding performance, low scattering properties and a low stickiness, and a lubricant or surface modifier (water repellent), a lubricating film, a magnetic recording medium and a magnetic recording device which make use of such a compound.

As a lubricant having low scattering properties, Japanese Patent Applications Laid-open No. 8-36741 and No. 8-36742 disclose a proposal of a crown ether compound comprising a perfluorooxyalkyl chain and a crown ether which are linked chiefly by an imino group. Such a compound, however, tends to absorb moisture, therefore tends to cause changes in lubricating performance as a result of moisture absorption, and is not desirable for lubricating films which are used in a highly humid atmosphere over a long period of time.

Accordingly, a second object of the present invention is to provide a fluorine-containing compound having a good sliding performance, low scattering properties and a low moisture absorption, and a lubricant or surface modifier (water repellent), a lubricating film, a magnetic recording medium and a magnetic recording device which make use of such a compound.

DISCLOSURE OF THE INVENTION

In order to achieve the first object, the present inventors synthesized various fluorine-containing compounds to make studies thereon. As a result, they have discovered that the first object can be achieved by a novel fluorine-containing compound having a perfluoropolyoxyalkylene chain in the molecule and in which atomic groups containing oxyethylene moieties are bonded to both terminals of this chain (hereinafter "first compound").

This compound of the present invention is liquid at normal temperature because it has in the molecule the perfluoropolyoxyalkylene chain, having a large molecular weight, and has a low volatility because it has the oxyethylene moieties. Hence, the use of the compound of the present invention makes it possible to maintain good lubricating performance over a longer period of time than ever.

The first compound, having oxyethylene moieties at both terminals of a perfluoropolyoxyalkylene chain, also has a lower stickiness than a compound having a perfluoropolyoxyalkylene chain to which one oxyethylene moiety is attached, and shows a small head stiction in the contact start-stop method (CSS method). Hence, its use in lubricating films is unlikely to cause a break due to sticking even when small-sized heads are used.

As a result of studies on conventional compounds having a perfluorooxyalkyl chain and a crown ether, the present inventors have also found that a high moisture absorption the compounds have is caused by the fact that they are connected by an imino linkage. The nitrogen atom in the imino linkage has so high a basicity that it reacts with $NO_x$, $SO_x$ etc. in air to change into a nitrate, a sulfite, a sulfate and so forth. Thus, the compound in which the imino linkage is present is, as a result of its contact with atmosphere for a long time, considered to become subject to absorbing water. Incidentally, $NO_x$ is contained in air in large quantities in the neighborhood of roads having a lot of traffic, and $SO_x$ in the neighborhood of thermal power stations, where moisture absorption tends to progress.

Accordingly, in order to achieve the second object, the present invention provides a novel fluorine-containing compound having both a perfluoropolyoxyalkyl chain and an oxyethylene moiety in the molecule which are linked by a linkage other than the imino linkage, as exemplified by an amide linkage, a sulfonamide linkage, an ester linkage or an ether linkage (hereinafter "second compound").

This second compound is also liquid at normal temperature because it has in the molecule the perfluoropolyoxyalkyl chain, having a large molecular weight, and has a low volatility because it has the oxyethylene moiety. It may also cause almost no change in lubricating performance due to moisture absorption. Hence, the use of the second compound makes it possible to maintain a good lubricating performance over a long period of time, and also this second compound has a superior storage stability.

A compound which is the first compound and in which the perfluoropolyoxyalkylene chain and the oxyethylene moieties are connected by linkages other than imino linkages is very useful because it can achieve both the first object and the second object mentioned above. Meanwhile, a compound which is the first compound and in which the perfluoropolyoxyalkylene chain and the oxyethylene moieties are connected by imino linkages is especially useful as a lubricant for cold districts because of its low pour point. Of course, it is also useful as a lubricant at places not exposed for long periods to the open air having a high humidity, because it has a good lubricating performance and has a low stickiness.

The present invention also provides a surface modifier (water repellent) that can improve water repellency of the surface to be treated, and a lubricant, both containing any of these fluorine-containing compounds of the present invention. Furthermore, the present invention provides a lubricating film containing these fluorine-containing compound of the present invention, a magnetic recording medium having the lubricating film, and a magnetic recording device including the recording medium.

BEST MODES FOR PRACTICING THE INVENTION

Figure 1:
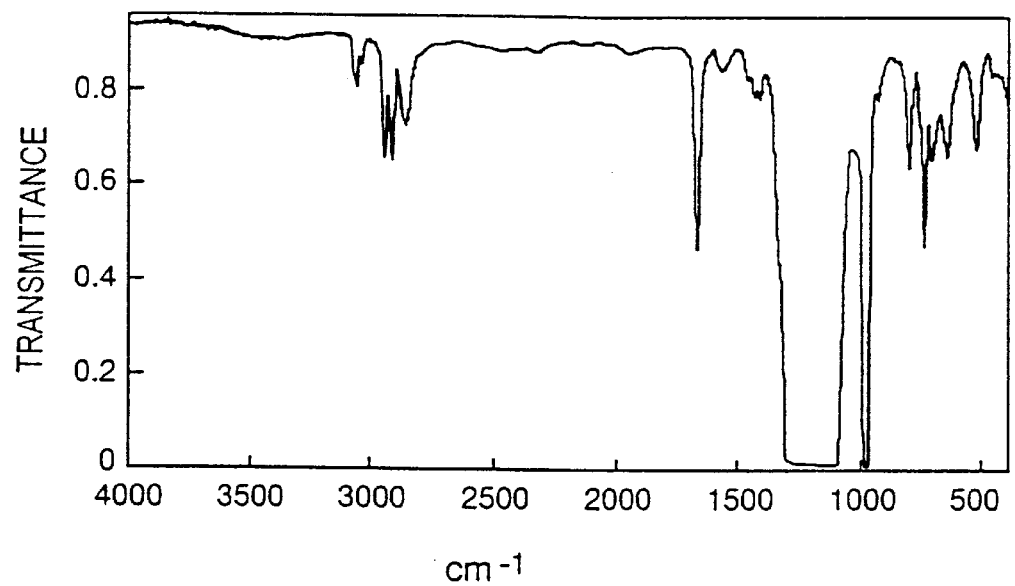
FIG. 1 shows an IR spectrum of compound 1.

The fluorine-containing compound of the present invention is a compound having a perfluoropolyoxyalkyl chain or a perfluoropolyoxyalkylene chain and a cyclic or non-cyclic oxyethylene moiety. The compound of the present invention, either of the first and second compounds, is liquid at normal temperature, has a low stickiness and has a superior lubricating performance, because it has a perfluoropolyoxyalkylene(or -alkyl) chain having a large molecular weight (molecular weight: 800 or more). The fluorine-containing compound of the present invention also has a low volatility and low scattering properties and maintains a superior lubricating performance over a long period of time.

The reason why the fluorine-containing compound of the present invention has low scattering properties is unclear, and is considered to be because it has the oxyethylene moiety in the molecule. The oxygen atom of the oxyethylene moiety forms an ether linkage. The oxygen atom of this type is known to have the action to associate chiefly with an alkali metal ion. Thus, it is presumed that an interaction takes place to a certain extent between a fluorine-containing compound coated on the surface of a magnetic recording medium and a metal such as iron or nickel present on the magnetic recording medium and such interaction leads to the low scattering properties.

A. First Compound

The first compound of the present invention has a structure represented by the following general formula (1):

$$X^1\text{—}R^1\text{—}X^1 \tag{1}$$

In the formula, $R^1$ is a perfluoropolyoxyalkylene chain having an average molecular weight of 800 or more, and $X^1$'s are each a group containing a polyether atomic group containing an oxyethylene moiety. The two $X^1$'s may be different from each other, but may preferably have the same structure in view of ease of synthesis.

The oxyethylene moiety contained in $X^1$ may be either cyclic or non-cyclic. The cyclic oxyethylene moiety is called a crown ether ring, and compounds having this ring are commonly called crown ethers. Compounds having a non-cyclic oxyethylene moiety are commonly called podands.

(a) Crown Ethers:

The compound in which the oxyethylene moiety represented by $X^1$ is cyclic may include the compound having a structure of the following general formula (2).

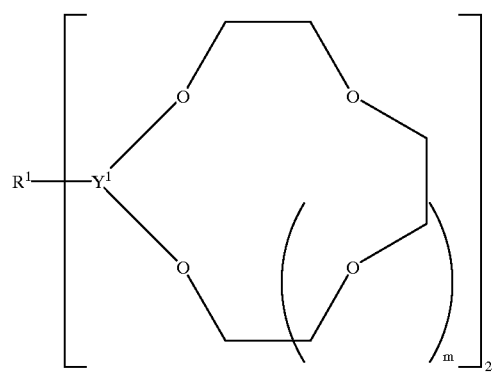

(2)

wherein $Y^1$ represents a trivalent group, and m represents an integer of 1 to 5. Preferred are compounds having as the $Y^1$ an organic group containing an aromatic ring that constitutes part of the crown ether ring, an organic group containing a methylidyne group that constitutes part of the crown ether ring or an organic group containing a nitrogen atom that constitutes part of the crown ether ring, i.e., compounds represented by the following general formulas (3) to (5):

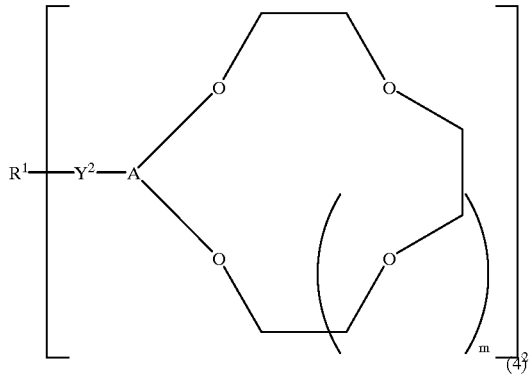

(3)

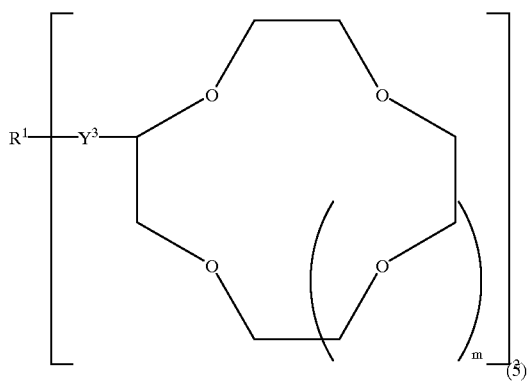

(4)

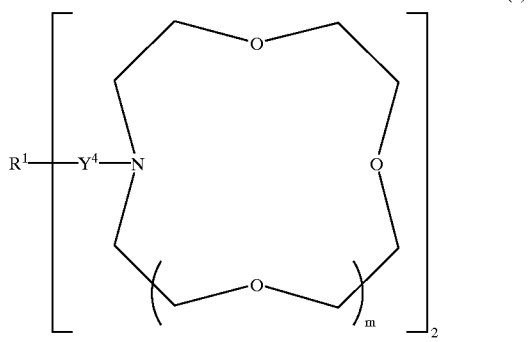

(5)

wherein A represents an aromatic ring. The two A's in one molecule may be different from each other, but may preferably have the same structure in view of ease of synthesis. $Y^2$ to $Y^4$ are each a divalent group, and m is an integer of 1 to 5.

A compound represented by the following structural formula (36) is particularly preferred because of its high resistance to a base and superior stability and lubricating performance:

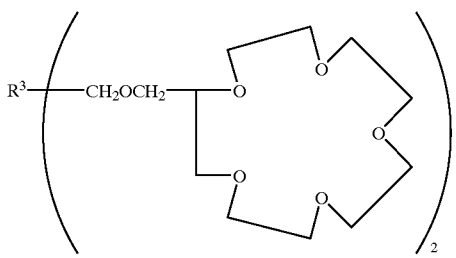

(36)

wherein $R^3$ is a perfluoropolyoxyalkylene chain having an average molecular weight of 800 or more, and may preferably be a copolymer group in which a repeating unit $CF_2CF_2O$ and a repeating unit $CF_2O$ are mixed at random in a ratio of from 0.6:1 to 1.2:1, having an average molecular weight of from 2,000 to 6,000.

(b) Podands:

The compound in which the oxyethylene moiety represented by $X^1$ is non-cyclic may include those having a structure represented by the following general formula (6):

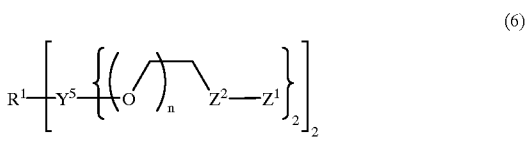

(6)

wherein $Z^1$ represents an alkyl group having 1 to 16 carbon atoms. The four Z's in one molecule may be different from each other, but may preferably have the same structure in view of ease of synthesis. $Z^2$ is a divalent group, $Y^5$ is a trivalent group, and n is an integer of 1 to 8.

Of the compounds represented by this general formula (6), a compound in which the $Y^5$ is an organic group containing an aromatic ring as part of the oxyethylene moiety (i.e., the part in { } in the formula (6)), that is, a compound represented by the following general formula (7), is particularly preferred because of its high solubility in organic solvents. In the formula, A and $Y^6$ represent an aromatic ring and a divalent group, respectively.

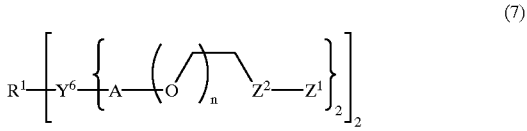

(7)

B. Second Compound

The second compound of the present invention is represented by the following general formula (8):

$R^2$—$X^2$ (8)

In the formula, $R^2$ is a perfluoropolyoxyalkyl chain having an average molecular weight of 800 or more, and $X^2$ is a group containing a polyether atomic group containing an oxyethylene moiety. The $X^2$ is constituted of an oxyethylene moiety and a portion linking to the $R^2$ (exclusive of the imino linkage). In this second compound too, the oxyethylene moiety may be either cyclic or non-cyclic.

(a) Crown Ethers:

The compound in which the oxyethylene moiety in $X^2$ is cyclic may include those having a structure represented by the following general formula (9):

(9)

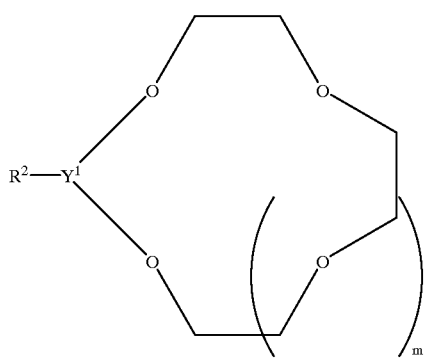

wherein $Y^1$ represents a trivalent group, and m represents an integer of 1 to 5. Preferred are compounds having as the $Y^1$ an organic group containing an aromatic ring that constitutes part of the crown ether ring, an organic group containing a methylidyne group that constitutes part of the crown ether ring or an organic group containing a nitrogen atom that constitutes part of the crown ether ring, i.e., compounds represented by the following general formulas (10) to (12). In the formulas, A represents an aromatic ring, $Y^2$ to $Y^4$ each represents a divalent group, and m represents an integer of 1 to 5.

(10)

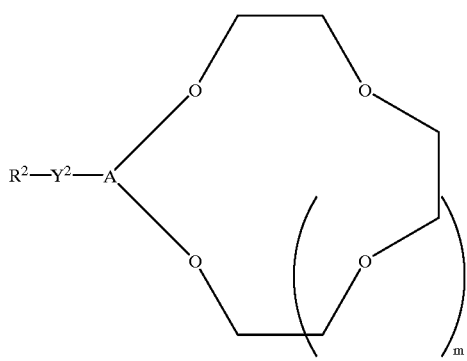

(11)

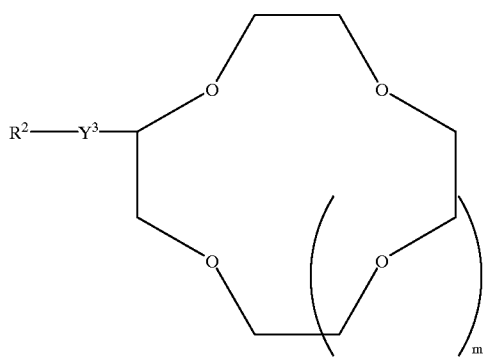

(12)

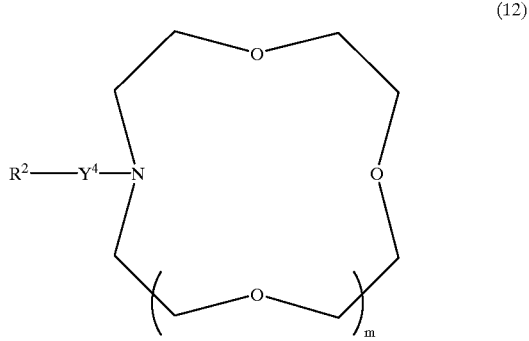

Like a compound represented by the following general formula (13) or (14), a compound in which a plurality of perfluoropolyoxyalkyl chains ($R^2$'s) are bonded to one crown ether ring may also be given as the second compound of the present invention:

(13)

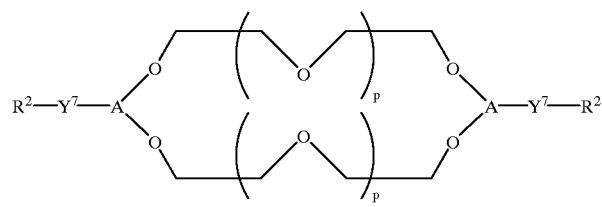

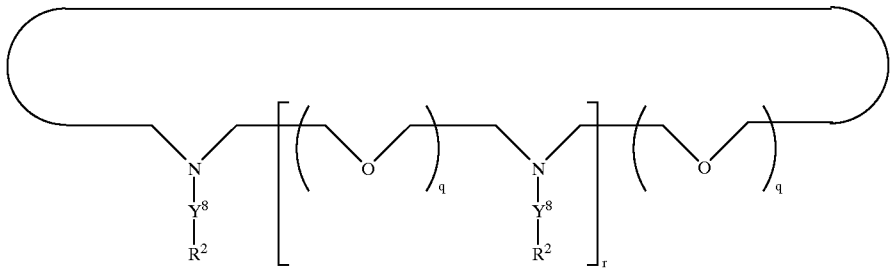

(14)

wherein A's each represent an aromatic ring, $Y^7$'s and $Y^8$'s are each a divalent group. Letter symbols p are each an integer of 1 to 5, letter symbols q are each an integer of 1 to 3, and r is an integer of 1 or 2. The two or more $R^2$'s, A's, $Y^7$'s or $Y^8$'s in one molecule may be different from each other, but may preferably have the same structure in view of ease of synthesis.

Of the compounds represented by the above general formula (14), particularly preferred are a compound represented by the following general formula (15) in which r is 1 and a compound represented by the following general formula (16) in which q's are each 1 and r is 2.

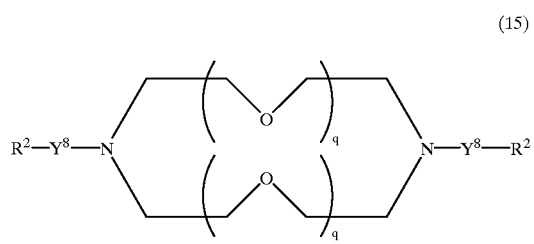

(15)

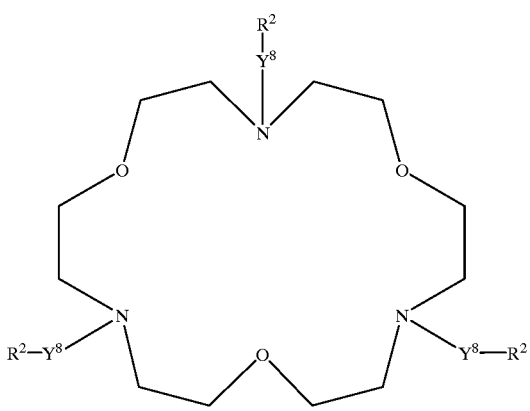

(16)

(b) Podands:

The compound in which the oxyethylene moiety represented by $X^2$ is non-cyclic may include those having a structure represented by the following general formula (17):

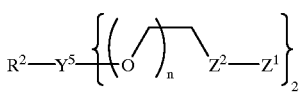

(17)

wherein $Z^1$ represents an alkyl group having 1 to 16 carbon atoms. The two $Z^1$'s in one molecule may be different from each other, but may preferably have the same structure in view of ease of synthesis. Letter symbol n is an integer of 1 to 8. $Z^2$ is a divalent group, and $Y^5$ is a trivalent group.

Of the compounds represented by the general formula (17), a compound in which the $Y^5$ is an organic group containing an aromatic ring as part of the oxyethylene moiety (i.e., the part in { } in the formula (17)), that is, a compound represented by the following general formula (18) is particularly preferred because of its high solubility in organic solvents. In the formula, A and $Y^6$ represent an aromatic ring and a divalent group, respectively.

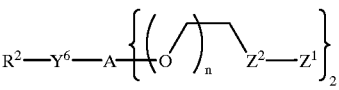

(18)

C. Details of Structure of Each Compound

Functional groups in each general formula described above will be described below specifically.

(a) $R^1$ and $R^2$:

In the above general formulas (1) to (7), $R^1$ is a perfluoropolyoxyalkylene chain having an average molecular weight of 800 or more. In the present specification, the perfluoropolyoxyalkylene chain refers to a divalent organic group consisting of a polymer in which one terminal is a perfluoroalkylene group and a repeating unit is an atomic group formed by combination of a perfluoroalkylene moiety with an oxygen atom, and is represented by the following general formula (19). In the formula, α is the number of repeating units present in one molecule. Letter symbol x is any desired natural number. The x may preferably be 1 to 5 in view of the need to ensure the fluidity of the compound, and particularly preferably 1 to 3 in view of the ease of obtaining starting materials.

$$-[C_{xIF2x}-O]_\alpha-C_xF_{2x}- \quad (19)$$

In the above general formulas (8) to (18), $R^2$ is a perfluoropolyoxyalkyl chain having an average molecular weight of 800 or more. In the present specification, the perfluoropolyoxyalkyl chain refers to a monovalent organic group consisting of a polymer in which one terminal is an atomic group formed by combination of a perfluoroalkyl group and an oxygen atom, the other terminal is a perfluoroalkylene group and a repeating unit is an atomic group formed by combination of a perfluoroalkylene moiety with an oxygen atom, and is represented by the following general formula (20). In the formula, β is the number of repeating units present in one molecule. Letter symbol x is any desired natural number. The x may preferably be 1 to 5 in view of the need to ensure the fluidity of the compound, and particularly preferably 1 to 3 in view of the ease of obtaining starting materials.

$$C_xF_{2x+1}-O-[C_xF_{2x}-O]\beta-C_xF_{2x}- \quad (20)$$

The groups represented by $R^1$ and $R^2$ may include a polymer having —CF(CF$_3$)CF$_2$O—, a copolymer having —CF(CF$_3$)CF$_2$O— and —(CF$_2$O)—, a copolymer having —CF$_2$CF$_2$O— and —CF$_2$O—, and a polymer having —CF$_2$CF$_2$CF$_2$O—, as the repeating unit [C$_x$F$_{2x}$—O]. The repeating units of a copolymer having two or more repeating units may be arranged in a random form or in a block.

The groups represented by $R^1$ and $R^2$ each have a molecular weight of 800 or more. This is because a fluorine-containing compound in which the groups represented by $R^1$ and $R^2$ each have a molecular weight less than 800 may have a low solubility in solvents having a perfluoroalkane structure. When coating films of the fluorine-containing compound of the present invention are formed, it is desirable to use as a solvent one having a perfluoroalkane structure. In order to form films with a stated layer thickness in a good operability, a solubility is required which is sufficient to prepare a solution having a certain concentration.

In order to improve the solubility in such a solvent having a perfluoroalkane structure, it is desirable for the $R^1$ or $R^2$ group to have a molecular weight as large as possible. Stated specifically, the group represented by $R^1$ or $R^2$ may preferably have a molecular weight of 2,000 or more. Also, the group represented by $R^1$ or $R^2$ may preferably have a molecular weight not more than 6,000 because the starting materials are then easily available.

(b) $Y^1$ to $Y^8$:

In the general formulas (2) to (7) and (9) to (18), $Y^1$ to $Y^8$ each constitute part of the linking portion between the perfluoropolyoxyalkyl(or -alkylene) chain and the oxyethylene moiety. As described previously, in order to control moisture absorption to a low level, the linkage that connects the perfluoropolyoxyalkyl(or -alkylene) chain with the oxyethylene moiety may preferably not be the imino linkage, having a high basicity. Thus, $Y^1$ to $Y^8$ may preferably be groups comprising an amide linkage, a sulfonamide linkage, an ether linkage or an ester linkage.

An alkylene group and/or an alkenylene group may also be introduced into the linkage which connects the perfluoropolyoxyalkyl(or -alkylene) chain with the oxyethylene moiety. This is preferable because the solubility in organic solvents can be improved.

Specific examples of $Y^2$ to $Y^4$ and $Y^6$ to $Y^8$ are listed below, where, of the two bond arms, the bond arm toward $R^1$ or $R^2$ is shown on the left side. The type of linkage which connects the perfluoropolyoxyalkyl(or -alkylene) chain with the oxyethylene moiety is shown in the parentheses. Rs represents a toluenesulfonyl group, a methanesulfonyl group or a naphthalenesulfonyl group.

$Y^2$, $Y^6$ and $Y^7$ may each preferably be —CONH— (an amide linkage), —CH$_2$NRs— (a sulfonamide linkage), —CH$_2$OCH$_2$— (an ether linkage, —CO$_2$CH$_2$— (an ester linkage), —CH$_2$OCO— (an ester linkage), —CH$_2$OCOCH$_2$CH$_2$— (an ester linkage) or —CH$_2$OCOCH=CH— (an ester linkage).

$Y^3$ may preferably be —CONHCH$_2$— (an amide linkage), —CH$_2$NRsCH$_2$— (a sulfonamide linkage), —CH$_2$OCH$_2$— (an ether linkage or —CO$_2$CH$_2$— (an ester linkage).

$Y^4$ and $Y^8$ may each preferably be a carbonyl group (an amide linkage).

Incidentally, the toluenesulfonyl group refers to a group having a structure consisting of —CH$_3$C$_6$H$_4$SO$_2$—, where C$_6$H$_4$ is a phenylene ring, and may include three types depending on the position of substitution of the CH$_3$ group, i.e., an o-toluenesulfonyl group, an m-toluenesulfonyl group and a p-toluenesulfonyl group, any of which is available. The methanesulfonyl group refers to a group having a structure comprising CH$_3$SO$_2$—. The naphthalenesulfonyl group refers to a residual group having a structure consisting of C$_{10}$H$_7$SO$_2$—, where C$_{10}$H$_7$ is a naphthalene ring, and may include two types depending on the position of linkage between the naphthalene ring and the SO$_2$ moiety, i.e., an α-naphthalenesulfonyl group and β-naphthalenesulfonyl group, any of which is available.

(c) A:

In the above general formulas (3), (7), (10), (13) and (18), A represents an aromatic ring. Here, the aromatic ring also includes a benzene ring, and besides heterocyclic rings such as furan and thiophene, and also includes condensed rings such as a naphthalene ring and an anthrathene ring. From the viewpoint of ensuring fluidity, the A may preferably have 4 to 14 carbon atoms.

The introduction of this aromatic ring into the molecule can achieve an improvement in solubility in organic solvents such as toluene.

(d) $Z^1$, $Z^2$:

In the general formulas (6), (7), (17) and (18), $Z^1$ is a terminal portion of the oxyethylene moiety (i.e., the part in { } in each formula).

If the terminal portion is hydrogen, the compound represented by any of the general formulas (6), (7), (14) and (15) has a low solubility in organic solvents such as solvents having a perfluoroalkane structure and methylene chloride. In order to improve the solubility in these solvents, it is desirable for the terminal portion $Z^1$ to be an alkyl group. The alkyl group may be any of straight-chain alkyl groups (e.g., a methyl group and an ethyl group) and those comprising a branch (e.g., an isopropyl group).

In the case when the perfluoropolyoxyalkyl(or -alkylene) chain has a molecular weight of about 800, the compound tends to have a very low solubility in the solvents having a perfluoroalkane structure, if the group represented by $Z^1$ has 17 or more carbon atoms. Accordingly, the group represented by $Z^1$ may preferably have 1 to 16 carbon atoms.

The linking portion $Z^2$ between this terminal $Z^1$ and the oxyethylene moiety is a divalent group, which may be a functional group such as —O—, —OCO—, —NHCO— (where, of the two bond arms, the bond arm toward the oxyethylene moiety is shown on the left side). Of these, linkages having no carbonyl group such as an ether linkage are preferred because they have a tendency to show a higher adsorptivity on metals and magnetic recording media or the like than linkages having a carbonyl group such as an amide linkage and an ester linkage.

(e) m to r:

Letter symbol m in the general formulas (2) to (5) and (9) to (12), p in the general formula (13) and q in the general formulas (14) and (15) are natural numbers which reflect the number of correspondence of the oxyethylene portion in the oxyethylene moiety (crown ether moiety). Letter symbol r in the general formula (14) is a natural number which reflects the number of correspondence of the azaethylene group in the oxyethylene moiety (crown ether moiety).

The fluorine-containing compound of the present invention may preferably have the oxyethylene portion or azaethylene group in a larger number because such a compound has a tendency to show a higher adsorptivity when coated on the metal surfaces or the surfaces of magnetic recording media. However, those having nine or more oxyethylene portions (or azaethylene groups) tend to give by-products in a large quantity when synthesized. Also, those having three or less oxyethylene portions may cause a great strain in molecules making them difficult to produce. Accordingly, m and p may each preferably be an integer of 1 to 5; q, 1 to 3; and r, 1 or 2.

Crown ether rings (i.e., cyclic polyethers) are commonly synthesized by reaction in which alkali metal ions fitting to the size of rings are used as casts. It is said that those having four oxyethylene portions (inclusive of azaethylene groups for those having azaethylene groups) readily fit to lithium ions; those having five, sodium ions; those having six, potassium ions or ammonium ions; those having seven, rubidium ions; and those having eight, cesium ions. Thus, the number of oxyethylene portions (or azaethylene groups) and the type of ions may be selected appropriately, whereby the synthesis can be made to proceed rapidly, the by-products can be made to occur less and the yield can be improved.

Letter symbol n in the general formulas (6), (7), (17) and (18) is a natural number which reflects the number of correspondence of the oxyethylene portion in the oxyethylene moiety (non-cyclic polyether moiety).

The fluorine-containing compound of the present invention may preferably have the oxyethylene portion in a larger number because such a compound has a tendency to show a higher adsorptivity when coated on the metal surfaces or the surfaces of magnetic recording media. Accordingly, n may preferably be 1 or more. On the other hand, if the compound has the oxyethylene portion present in too a large number, it tends to have a low solubility in the solvents having a perfluoroalkane structure. In particular, if n is 9 or more, the compound may have an extremely low solubility especially when the perfluoropolyoxyalkyl(or -alkylene) chain has a small molecular weight. Accordingly, n may preferably be 8 or less.

D. Synthesis Process

Basically, the fluorine-containing compound of the present invention can be obtained by allowing a compound having the perfluoropolyoxyalkyl(or -alkylene) chain to react with a compound having the oxyethylene moiety (crown ether structure or podand structure).

(a) Compound having the perfluoropolyoxyalkyl(or -alkylene) chain:

In the synthesis of the fluorine-containing compound of the present invention, used as materials for introducing the group represented by $R^1$ or $R^2$ into the molecule are, e.g., compound having the perfluoropolyoxyalkyl(or -alkylene) chain and having, at a terminal of the chain, a functional group for coupling with a compound having the oxyethylene moiety, such as a halogen atom, a carboxyl group or a hydroxyl group.

Of the materials for introducing the perfluoropolyoxyalkyl(or -alkylene) chain, those having a carboxyl group at a terminal can be linked with the atomic group containing the oxyethylene moiety, which is the other constituent of the fluorine-containing compound of the present invention, by forming an amide linkage or an ester linkage; and those having a hydroxyl group at a terminal, by forming an ether linkage or an ester linkage. Thus, the fluorine-containing compound of the present invention can be obtained.

Use of those having a halogen atom at a terminal makes it possible to also obtain the fluorine-containing compound of the present invention with ease, having, e.g., a —CH$_2$NRs—, —CH$_2$OCH$_2$— or —CO— linkage at the linking portion between the $R^1$ or $R^2$ and the oxyethylene moiety. The introduction of a halogen into the compound having the perfluoropolyoxyalkyl(or -alkylene) chain may be made using, e.g., thionyl chloride or oxalyl chloride.

As materials for introducing the $R^1$ or $R^2$ group to synthesize the fluorine-containing compound of the present invention, usable are, stated specifically, Krytox (repeating unit: —CF(CF$_3$)CF$_2$O—), available from Du Pont; Fombrin or Fombrin Z-Series (repeating units: —CF(CF$_3$)CF$_2$O— and —CF$_2$O—, or —CF$_2$CF$_2$O— and —CF$_2$O—), available from Ausimont Co.; Demnum (repeating unit: —CF$_2$CF$_2$CF$_2$O—), available from Daikin Kogyo Co.; and appropriately modified products of these.

(b) Compound Having the Oxyethylene Moiety:

In the synthesis of the fluorine-containing compound of the present invention, used as materials for introducing the oxyethylene moiety into the molecule are, e.g., those having the oxyethylene moiety (crown ether moiety or podand moiety) and a functional group for coupling with the material for introducing the group represented by $R^1$ or $R^2$, such as an amino group, a carboxyl group and a hydroxyl group.

The functional group for the coupling may be appropriately selected in accordance with the linking moieties ($Y^1$ to $Y^8$) in the fluorine-containing compound to be synthesized. For example, an amino group may be used for the synthesis of a compound having an amide group at the linking moiety; an —NHRs group may be used for the synthesis of a compound having a sulfonamide group; and a hydroxyalkyl group, carboxyl group or acyl halide group may be used for the synthesis of a compound having an ether linkage or ester linkage.

Specific examples of materials for introducing the oxyethylene moiety, used to synthesize the compound represented by the general formula (3) or (10) when A is a benzene ring will be listed below. To synthesize the compound in which $Y^2$ is —CONH—, an aminobenzo-crown ether compound is used. To synthesize the compound in which $Y^2$ is —CH$_2$NRs—, an NHRs-crown ether, i.e., an aminobenzo-crown ether compound having a toluenesulfonyl group, a methanesulfonyl group or a naphthalenesulfonyl group being substituted for one of the hydrogen atoms of its amino group, is used. This compound can be synthesized by using the aminobenzo-crown ether compound and toluenesulfonyl chloride, methanesulfonyl chloride or naphthalenesulfonyl chloride. To synthesize the compound in which $Y^2$ is —CO$_2$CH$_2$— or —CH$_2$OCH$_2$—, a hydroxymethylbenzo-crown ether compound is used. This compound can be obtained by, e.g., hydrogenating a formylbenzo-crown ether compound with sodium boron hydride. To synthesize the compound in which $Y^2$ is —CH$_2$OCO—, a carboxybenzo-crown ether compound is used. This compound can be obtained by, e.g., oxidizing a formylbenzo-crown ether compound with silver nitrate. To synthesize the compound in which $Y^2$ is —CH$_2$OCOCH=CH—, a 2-carboxyvinylbenzo-crown ether compound is used. This compound can be obtained by, e.g., allowing a formylbenzo-crown ether compound to react with malonic acid. To synthesize the compound in which $Y^2$ is —CH$_2$OCOCH$_2$CH$_2$—, a 2-carboxyethylbenzo-crown ether compound is used. This compound can be obtained by hydrogenating the 2-carboxyvinylbenzo-crown ether compound in the presence of platinum oxide or the like as a catalyst.

Specific examples of materials for introducing the oxyethylene moiety, used to synthesize the compound represented by the general formula (4) or (11) will be listed below. To synthesize the compound in which $Y^3$ is —CONHCH$_2$—, an aminomethyl-crown ether compound is used. To synthesize the compound in which $Y^3$ is —CH$_2$NRsCH$_2$—, an NCH$_3$Rs-crown ether compound, i.e., an aminomethyl-crown ether compound having a toluenesulfonyl group, a methanesulfonyl group or a naphthalenesulfonyl group being substituted for the hydrogen atoms of its amino group, is used. To synthesize the compound in which $Y^3$ is —CO$_2$CH$_2$— or —CH$_2$OCH$_2$—, a hydroxymethyl-crown ether compound is used. To synthesize the compound in which $Y^3$ is —CH$_3$OCO—, a haloformyl-crown ether compound is used. This compound can be obtained by halogenating the carboxyl group of a carboxyl-crown ether compound by the use of thionyl chloride or oxalyl chloride.

Specific examples of materials for introducing the oxyethylene moiety, used to synthesize the compound represented by the general formula (13) when both A's are benzene rings will be listed below. To synthesize the compound in which $Y^7$ is —CONH—, a di(aminobenzo)-crown ether compound is used. This compound can be synthesized by nitrating a dibenzo-crown ether compound followed by reduction (see W. M. Feigenbaum and R. H. Michel, "Journal of Polymer Science", p.817, vol. 9, part A-1, (1970)). To synthesize the compound in which $Y^7$ is —$CH_2NRs$—, a di(aminobenzo)-crown ether compound having a toluenesulfonyl group, a methanesulfonyl group or a naphthalenesulfonyl group being substituted for one hydrogen atom in each of the two amino groups, is used. To synthesize the compound in which $Y^7$ is —$CO_2CH_2$— or —$CH_2OCH_2$—, a di(hydroxymethylbenzo)-crown ether compound is used. To synthesize the compound in which $Y^7$ is —$CH_2OCO$—, a di{(haloformyl)benzo}-crown ether compound is used. To synthesize the compound in which $Y^7$ is —$CH_2OCOCH=CH$—, a di({haloformyl)vinylbenzo}-crown ether compound is used. To synthesize the compound in which $Y^7$ is —$CH_2OCOCH_2CH_2$—, a di{(haloformyl)ethylbenzo}-crown ether compound is used.

In the synthesis of the fluorine-containing compound represented by the general formula (5), (12) or (14), as materials for introducing the oxyethylene moiety, used are those in which the oxyethylene moiety is formed as a crown ether ring containing a nitrogen atom. In this instance too, the functional group for the coupling may be appropriately selected in accordance with the linking moieties ($Y^4$, $Y^8$) in the fluorine-containing compound to be synthesized and in the same manner as the examples described above.

The number of nitrogen atoms in the crown ether ring may also be appropriately selected in accordance with the number of nitrogen atoms in the ring of the compound to be synthesized. For example, to synthesize the compound represented by the general formula (5) or (12), an aza-crown ether compound is used. In the case of the compound represented by the general formula (14), a diaza-crown ether compound and a triaza-crown ether compound are used when r is 1 and when r is 2, respectively.

The aza-crown compound may include 1-aza-15-crown-5, 1-aza-18-crown-6 and 1-aza-24-crown-8. The diazacrown compound may include 1,7,10,16-tetraoxa-4,13-diazacyclooctadecane. The triaza-crown compound may include 1,7,13-trioxa-4,10,16-triazacyclooctadecane.

The 1,7,13-trioxa-4,10,16-triazacyclooctadecane can be synthesized by a process disclosed in, e.g., the publication "Journal of the Organic Chemistry", by S.A.G. Hogberg and D. J. Cram, p.151, Vol. 40 (1975).

Materials for introducing the oxyethylene moiety, used to synthesize the compound represented by the general formula (7) or (18) when A is a benzene ring may include, e.g., 1,2-bis(2-methoxyethoxy)-4-aminobenzene, 1,2-bis(3,6,9-trioxahenicocyloxy)-4-aminobenzene, and 1,2-bis(3,6,9,12,15,18,21,24-octaoxahexatriacontyloxy)-4-aminobenzene.

The 1,2-bis(2-methoxyethoxy)-4-aminobenzene can be synthesized by first allowing catechol to react with 2-chloroethyl methyl ether to synthesize 1,2-bis(2-methoxyethoxy)benzene, then allowing it to react with nitric acid to effect nitration at the 4-position of the benzene ring, and thereafter reducing its nitro group to an amino group.

The 1,2-bis(3,6,9-trioxahenicocyloxy)-4-aminobenzene or 1,2-bis(3,6,9,12,15,18,21,24-octaoxahexatriacontyloxy)-4-aminobenzene can be synthesized in the same manner as the above except that the 2-chloroethyl methyl ether is replaced with a compound obtained by chlorinating the hydroxyl group of tri(or octa)ethylene glycol mono-n-dodecyl ether.

(c) Introduction of an Alkylene or Alkenylene Group:

As stated previously, it is desirable for improvement of the solubility in organic solvent to introduce an alkylene group and/or an alkenylene group into the linkage which connects the perfluoropolyoxyalkyl(or -alkylene) chain with the oxyethylene moiety. An example of how to introduce it will be described below, giving an example of synthesizing a compound having an ester linkage at the linking portion.

As a first example, a compound having the desired alkylene group and/or alkenylene group between $R^1$ or $R^2$ (or the oxyethylene moiety) and a hydroxyl group may be esterified with a carboxylic acid having the oxyethylene moiety (or $R^1$ or $R^2$), and thus a compound can be obtained in which the desired alkylene group and/or alkenylene group and the ester linkage have been introduced between $R^1$ or $R^2$ and the oxyethylene moiety.

As another example, the carboxyl group of a carboxylic acid having the oxyethylene moiety (or $R^1$ or $R^2$) may be reduced with $LiAlH_4$ or the like to make it into a $CH_2OH$ group, and this may be converted to $CH=CH—COOH$ by a process similar to a Perkin reaction and esterified with an alcohol having the group represented by $R^1$ or $R^2$ (or the oxyethylene moiety), thus a compound can be obtained in which a —$CH=CH—COO$— group has been introduced between $R^1$ or $R^2$ and the oxyethylene moiety.

As still another example, the —$CH=CH—COOH$ group obtained by the above reaction similar to a Perkin reaction may be hydrogenated in the presence of platinum oxide or the like as a catalyst to convert it to —$CH_2CH_2$—$COOH$, and this may be esterified with an alcohol having the group represented by $R^1$ or $R^2$ (or the oxyethylene moiety), and thus a compound can be obtained in which the —$CH_2CH_2$—$COO$— group has been introduced between $R^1$ or $R^2$ and the oxyethylene moiety.

(d) Reaction Conditions:

In the synthesis of the fluorine-containing compound of the present invention, the solvents having a perfluoroalkane as a basic structure may be used as solvents for material compounds having the perfluoropolyoxyalkyl(or -alkylene) chain. Stated specifically, they may include FC-72, FC-75 and FC-77, available from 3M. Also, solvents for material compounds having the oxyethylene moiety may include methylene chloride, chloroform, tetrahydrofuran and diethyl ether.

Coupling reaction temperature may preferably be close to a boiling point temperature of a solvent having a lower boiling point of two solvents used. Reaction time may differ depending on the type of materials and the type of reaction, and may preferably be about 12 to 120 hours. Purification may be carried out by a conventional method.

E. Uses and How to Use

The fluorine-containing compound of the present invention can be used as a surface modifier which modifies surface properties (such as lubricity, water repellency, waterproofness and dust- or trash-proofness) of various media. The surface modifier of the present invention may have any form so long as it contains the fluorine-containing compound of the present invention. It may consist of only the fluorine-containing compound of the present invention, or may be in the form of a solution or suspension prepared by dissolving or suspending this compound in solvent.

In the case when the fluorine-containing compound of the present invention is used in the form of its solution or suspension, the solution or suspension may be coated on the surface to be treated, followed by vaporization of solvent for its removal, whereby a film comprising the fluorine-containing compound of the present invention can be formed.

At present, the load applied to the head is about 1 g to about 10 g, whereas the rigidity of the head shows a tendency to lower because the head used is tends to be small-sized in order to make the density higher. The head may break at a sticking force or frictional force of about 15 g or above. Hence, the coefficient of kinetic friction and coefficient of static friction with the head may preferably be 1.5 or less, and may particularly preferably be less than 1.0 if possible, taking account of a margin.

In order to improve the lubricity of the magnetic recording medium against the head, the lubricating film may preferably be formed in a thickness not larger than 30 nm on average. This is because, if it has too large a thickness, there is a possibility of an increase in the coefficient of static friction between the medium and the head. If it is too small, there is a possibility that the lubricant becomes almost run short at some parts as a result of long-term sliding. If this occurs, the frictional force at that part becomes so extraordinarily great as to cause break of the head or disk in some cases. Accordingly, the lubricating film may preferably have a thickness not smaller than 0.5 nm on average. To form such a thin film, the film may preferably be formed by such coating as mentioned above because of its readiness to control layer thickness.

When the film is formed by such a method, it is necessary to carry out post-treatment for removing the solvent after the lubricant has been coated. The manner of post-treatment may differ depending on the boiling point or vaporization heat of the solvent used. For example, a coating may be dried by leaving it at normal temperature under normal pressure or reduced pressure, or by heating it slightly. When thus dried, there is a possibility that the film is apt to absorb the moisture in air if a solvent having a large vaporization heat is used. Also, it is more desirable to use a solvent which volatilizes immediately as far as possible at normal temperature and under normal pressure after the coating, taking account of operability and prevention of moisture absorption. If, however, the solvent has too low a boiling point, it may volatilize too easily, bringing about a possibility that it becomes difficult to control solvent concentration. Accordingly, the solvent to be used may preferably be one having a small vaporization heat (50 cal/g or below) and a boiling point of from about 50 to 110° C. Such a solvent may include, e.g., solvents having a perfluoroalkane structure, and solvents having a structure of a perfluoroalkane in which a methoxy group or a hydrogen atom is substituted for some of the fluorine atoms.

The surface modifier of the present invention is especially suited as a lubricant for magnetic disk surfaces, bearings and various gears. It is also suited for its use as a water repellent or waterproofing agent for heat dissipation fins of air conditioners, various indoor or outdoor antennas (VHF-UHF antennas or parabolic antennas for television receivers), various cables such as power transmission lines and telephone lines, gliding faces of skis and snowboards, surfaces of diving suits and skiwear, exteriors of airplanes and ships, exterior wall of buildings, and so forth. It may also be used as dust- or trash-proofing agents for printed matter, art works and interior materials (such as wall paper).

F. Magnetic Recording Medium

The fluorine-containing compound of the present invention is especially suited for its use as a lubricating film for magnetic recording media. A magnetic recording medium of the present invention which has such a lubricating film of the present invention will be described below.

The magnetic recording medium of the present invention is a recording medium on and/or from which information can be written and/or read by the aid of magnetism, as exemplified by magnetic disks, floppy disks and magneto-optical disks, used as external memories of computers, word processors and the like. Usually, magnetic disks have a size of from about 1 inch to 14 inches, to which the present invention is by no means limited. In the case of hard disk devices, a large recording capacity can be ensured by piling up one to several magnetic disks.

In order to ensure as large a capacity as possible in one disk, it is more desirable for the distance between the disk and the head to be smaller. According to the lubricant of the present invention, in view of its performance, this distance can be made 40 nm or smaller on average. Since, however, the actual capacity also depends on the performance of the head or disk, the capacity can not be determined only from this distance.

The magnetic recording medium of the present invention usually has a non-magnetic support, at least one magnetic material layer provided on the non-magnetic support, and the above lubricating film provided as the outermost layer. The magnetic recording medium of the present invention is by no means limited to such a constitution. Optionally, it may be provided with a protective layer between the magnetic material layer and the lubricating film, and may also be provided with an additional layer (comprising, e.g., a complex or oxide containing Ni, Cr or Zn or a metal complex containing phosphorus) between the support and the magnetic material layer or between the magnetic material layer and the protective layer for the purpose of improving adhesion of these layers. A plurality of the magnetic material layers may also be provided.

As the non-magnetic support, a substrate comprising, e.g., an alloy of a metal such as Al, a ceramic such as glass or an organic high-polymer compound such as polycarbonate or polystyrene is used. The magnetic material layer is a layer comprising, e.g., an alloy constituted chiefly of Fe, Co or Ni or oxide thereof, and may also be a multi-layered film. As the protective layer, a film comprising carbon, SiC or $SiO_2$ may be used. Also, the lubricating film is a thin film containing at least one fluorine-containing compound of the present invention, and may preferably have a thickness of 30 nm or less on average in order to control the coefficient of static friction acting between it and the head to a low level.

Thus, since the lubricating film comprising the fluorine-containing compound of the present invention which is a good lubricant having a superior lubricating performance, a low scattering and a low stickiness is provided as the outermost layer, the magnetic recording medium of the present invention can ensure good sliding with respect to the magnetic head, and can prevent any breakage due to sticking even when a small-sized magnetic head is used.

As the non-magnetic support, from the viewpoint of mechanical strength, potassium glass containing potassium in a large quantity may preferably be used. Also when sodium glass is used as the non-magnetic support, the sodium on the surface may be replaced with potassium so long as the sodium is contained to some extent, whereby the necessary mechanical strength can be attained. On the other hand, if the glass contains sodium and potassium in too large a quantity, it may have a low toughness and tend to break at a small impact. Accordingly, the sodium and potassium in the non-magnetic support may preferably be in a content of from about 5 to 20% by weight based on the weight of the whole glass, as a total of sodium content and potassium content after the sodium on the surface has been. replaced with potassium.

In the case when a glass substrate containing potassium and/or sodium is used as the non-magnetic support, it is foreseen that alkali metals (ions) contained in glass pass through the magnetic layer and protective layer to reach the lubricating layer in the form of strongly basic hydroxides. Of the fluorine-containing compound of the present invention, the compound with a linkage being tough to bases, such as an amide linkage, a sulfonamide linkage or an ether linkage, is used at the connecting portion between the oxyethylene moiety and the perfluoropolyoxyalkyl(or -alkylene) moiety is particularly preferred because it may be hardly decomposed even by such strongly basic hydroxides (or alkali metal ions).

The present invention will be described below in greater detail by giving Examples. The scope of the present invention is by no means limited by these Examples.

SYNTHESIS EXAMPLE 1

A compound represented by the following structural formula (21) (hereinafter "compound 1") was synthesized in the following manner. This compound 1 is the compound represented by the general formula (3) where $R^1$ is $R^3$, $Y^2$ is —CONH—, A is a benzene ring and m is 2.

In the structural formula (21), $R^3$ is a copolymer group in which the repeating unit $CF_2CF_2O$ and the repeating unit $CF_2O$ are mixed at random in a ratio of from 0.6:1 to 1.2:1.

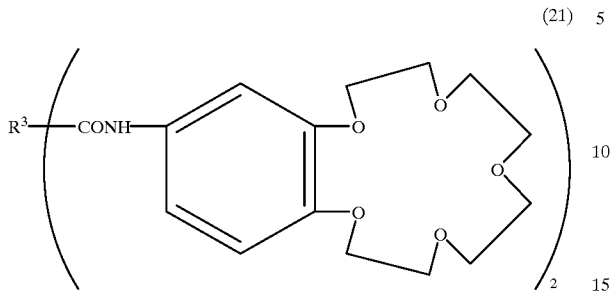

First, 20 parts by weight of Fombrin Z-DIAC (average molecular weight: 4,000), available from Ausimont Co., was dissolved in 200 parts by weight of FC-72, available from 3M, and the solution obtained was cooled to 0° C. Then, 8 parts by weight of 4'-aminobenzo-15-crown-5 was dissolved in 50 parts by weight of methylene chloride, and the solution obtained was cooled to 0° C., which was thereafter added to the above FC-72 solution of Z-DIAC. To the solution thus obtained, 6 parts by weight of dicyclohexyl carbodiimide (hereinafter "DCC") was added, and the reaction solution was stirred for 8 hours while keeping it at 0° C. and for 40 hours at room temperature, which was then subsequently left for 12 hours at room temperature.

Next, from the reaction solution separated into two liquid phases, the upper-phase methylene chloride solution and the solid matter (mostly a reaction product of DCC) gathering at the upper part of an FC-72 phase (the lower phase) were removed, and 50 parts by weight of methylene chloride was again added. The mixture obtained was stirred for 2 hours at room temperature, and thereafter subsequently left for 12 hours at room temperature.

The upper-phase methylene chloride solution and the solid matter gathering slightly at the upper part of the FC-72 phase were removed, and the FC-72 of the remaining FC-72 solution was volatilized using an evaporator. Thereafter, FC-72 still remaining slightly was volatilized using a vacuum pump. Thus, the desired compound 1 (21 parts by weight) was obtained.

An infrared (IR) spectrum of the compound 1 is shown in FIG. 1. In the starting material Z-DIAC, the signal due to the CO stretching vibration of the carboxyl group was seen at 1,780 cm$^{-1}$, whereas, in the compound 1 obtained, it was shifted to 1,710 cm$^{-1}$ because the carboxyl group was converted to an amide (—CONH—).

In a $^{19}F$ nuclear magnetic resonance ($^{19}F$-NMR) spectrum, the positions (−79.9 ppm and −81.7 ppm) of signals due to $CF_2$ adjoining to the carbonyl carbon in the Z-DIAC differed only very slightly from the positions (−79.9 ppm and −81.6 ppm) of signals due to $CF_2$ in the compound 1. In a proton nuclear magnetic resonance ($^1H$-NMR) spectrum, the signal of the carboxyl group of Z-DIAC had too low a peak intensity to be observed. Thus, very little difference was seen between the compound obtained and the starting material in NMR. Accordingly, in the following Synthesis Examples, only the results of IR are shown unless particularly noted.

SYNTHESIS EXAMPLE 2

A compound represented by the following structural formula (22) (hereinafter "compound 2") was obtained in the same manner as in Synthesis Example 1 except that the 4'-aminobenzo-15-crown-5 was replaced with 7 parts by weight of 4'-aminobenzo-12-crown-4. Yield was 20 parts by weight.

This compound 2 is the compound represented by the general formula (3) where $R^1$ is $R^3$, $Y^2$ is —CONH—, A is a benzene ring and m is 1.

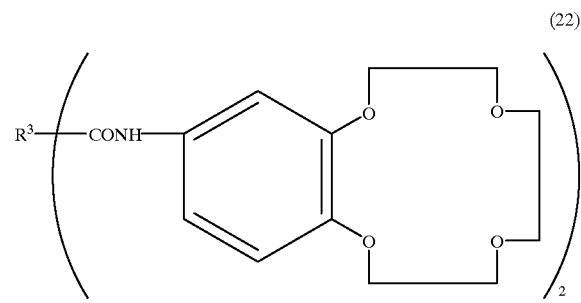

The compound 2 thus obtained showed substantially the same IR spectrum as that of the compound 1.

The 4'-aminobenzo-12-crown-4 was obtained by nitrating benzo-12-crown-4 followed by reduction, in the same manner as the process of synthesizing 4'-aminobenzo-15-crown-5, disclosed in R. Ungaro, B. El Haj and J. Smid, "Journal of the American Chemical Society", p.5198, Vol. 98 (1976).

SYNTHESIS EXAMPLE 3

A compound represented by the following structural formula (23) (hereinafter "compound 3") was obtained in the same manner as in Synthesis Example 1 except that the 4'-aminobenzo-15-crown-5 was replaced with 12 parts by weight of 4'-aminobenzo-24-crown-8. Yield was 22 parts by weight.

This compound 3 is the compound represented by the general formula (3) where $R^1$ is $R^3$, $Y^2$ is —CONH—, A is a benzene ring and m is 5.

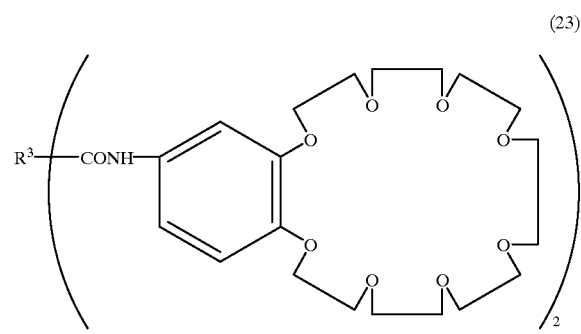

The compound 3 thus obtained exhibited substantially the same IR spectrum as that of the compound 1.

The 4'-aminobenzo-24-crown-8 was obtained by nitrating benzo-24-crown-8 followed by reduction, in the same manner as in Synthesis Example 2.

SYNTHESIS EXAMPLE 4

A fluorine-containing compound represented by the following structural formula (24) (hereinafter "compound 4") was synthesized in the following manner. This compound is represented by the general formula (3) where $R^1$ is $R^3$, $Y^2$ is —CH$_2$N(Ts)—, A is a benzene ring and m is 2. Here, Ts is a p-toluenesulfonyl group.

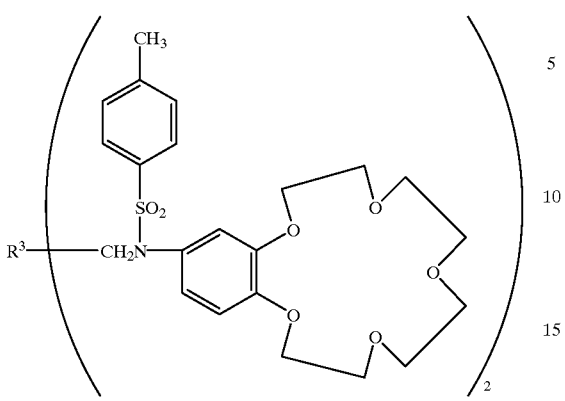

(i) Synthesis of Chain Compound:

In the first place, a perfluoropolyoxyalkylene chain compound whose terminal is formed of $CH_2Br$ (hereinafter "compound 4'") was synthesized.

First, 20 parts by weight of Fombrin Z-DOL (average molecular weight: 4,000), available from Ausimont Co., was dissolved in 100 parts by weight of Vertrel XF, available from Du Pont, and then the solution obtained was cooled to 0° C. To this solution, 8 parts by weight of thionyl bromide was added, and the mixture obtained was stirred for 1 hour at room temperature and subsequently stirred for 8 hours while refluxing it. Thereafter, the reaction solution was cooled to room temperature, and Vertrel XF and the excess thionyl bromide were volatilized by means of an evaporator to obtain 20 parts by weight of the compound 4'.

(ii) Synthesis of Crown Ether Compound:

Next, a compound of 4'-aminobenzo-15-crown-5 which a p-toluenesulfonyl group was introduced to its amino group (hereinafter "compound 4''") was synthesized.

First, 10 parts by weight of 4'-aminobenzo-15-crown-5 was dissolved in 50 parts by weight of pyridine, and thereafter the solution obtained was cooled to 0° C. To this solution, 8 parts by weight of p-toluenesulfonyl chloride was added, and the mixture obtained was stirred for 1 hour at room temperature, and subsequently, for 2 hours while refluxing it. Thereafter, the reaction solution was cooled to room temperature, and poured into 500 parts by weight of 10% hydrochloric acid. The solid thus deposited was collected by filtration, and then thoroughly washed with 10% hydrochloric acid to remove the pyridine. Thereafter, it was thoroughly washed with water until the washing turned neutral, followed by recrystallization with ethyl acetate and n-hexane to obtain 12 parts by weight of the compound 4''.

(iii) Coupling:

The compound 4' and compound 4'' obtained as described above were reacted in the following way to obtain the desired compound 4.

First, the compound 4' in its total weight (20 parts by weight) which was obtained by the above reaction was dissolved in 200 parts by weight of FC-75, available from 3M. To the solution thus obtained, the compound 4'' in its total weight (12 parts by weight) obtained by the above reaction, 4 parts by weight of potassium carbonate and 50 parts by weight of ethanol were added, and the mixture obtained was stirred for 8 hours while refluxing it, and then left quietly for 12 hours at room temperature. Thereafter, the upper-phase ethanol solution and the solid matter composed chiefly of potassium carbonate were removed.

Next, to the lower-phase solution thus obtained, 50 parts by weight of methylene chloride was added, and the mixture obtained was stirred for 1 hour at room temperature and then left quietly for 12 hours. Thereafter, the upper-phase methylene chloride solution was removed. FC-75 of the remaining FC-75 solution was volatilized using an evaporator, and thereafter FC-75 still remaining slightly was volatilized using a vacuum pump. Thus, 20 parts by weight of the desired compound 4 was obtained.

The compound 4 thus obtained exhibited substantially the same IR spectrum as that of the compound 1 except that absorption considered to be due to the NH stretching vibration of the sulfonamide was seen at 3,200 $cm^{-1}$ and the absorption at 1,710 $cm^{-1}$ due to the CO stretching vibration of the amide and absorption at 1,550 $cm^{-1}$ due to the NH bending vibration had disappeared.

SYNTHESIS EXAMPLE 5

A fluorine-containing compound represented by the following structural formula (25) (hereinafter "compound 5") was obtained in the same manner as in Synthesis Example 4 except that the p-toluenesulfonyl chloride was replaced with 10 parts by weight of β-naphthalenesulfonyl chloride. Yield was 20 parts by weight.

This compound is represented by the general formula (3) where $R^1$ is $R^3$, $Y^2$ is —$CH_2N(Ns)$—, A is a benzene ring and m is 2. Here, Ns is a β-naphthalenesulfonyl group.

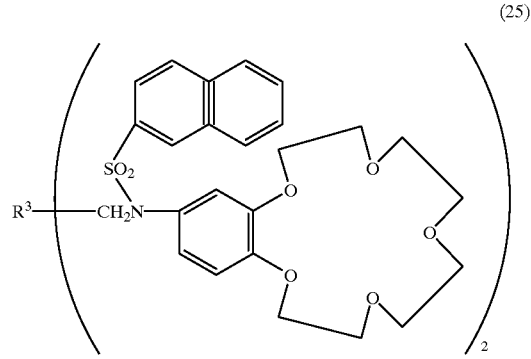

The compound 5 thus obtained showed substantially the same IR spectrum as that of the compound 4.

SYNTHESIS EXAMPLE 6

A fluorine-containing compound represented by the following structural formula (26) (hereinafter "compound 5") was obtained in the same manner as in Synthesis Example 4 except that the p-toluenesulfonyl chloride was replaced with 5 parts by weight of methanesulfonyl chloride. Yield was 18 parts by weight.

This compound is represented by the general formula (3) where $R^1$ is $R^3$, $Y^2$ is —$CH_2N(Ms)$—, A is a benzene ring and m is 2. Here, Ms is a methanesulfonyl group.

(26)

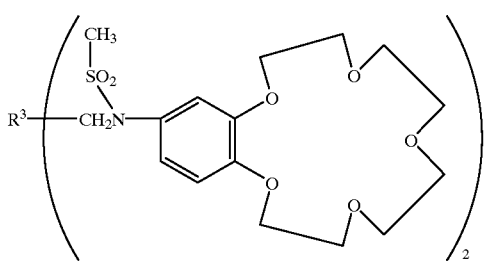

The compound 6 thus obtained showed substantially the same IR spectrum as that of the compound 4.

SYNTHESIS EXAMPLE 7

A fluorine-containing compound represented by the following structural formula (27) (hereinafter "compound 7") was synthesized in the following manner. This compound is represented by the general formula (3) where $R^1$ is $R^3$, $Y^2$ is —$CO_2CH_2$—, A is a benzene ring and m is 2.

(27)

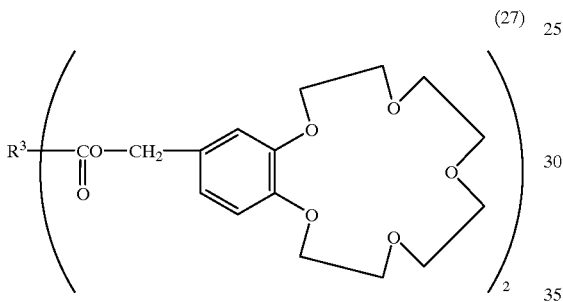

First, 20 parts by weight of Fombrin Z-DIAC (average molecular weight: 4,000), available from Ausimont Co., was dissolved in 200 parts by weight of FC-72, available from 3M, and the solution obtained was cooled to 0° C.

Next, 4 parts by weight of 4'-(hydroxymethyl)benzo-15-crown-5 was dissolved in 50 parts by weight of methylene chloride, and the solution obtained was cooled to 0° C., which was thereafter added to the above solution of Z-DIAC.

To the solution thus obtained, 4 parts by weight of DCC was added, and the reaction solution was stirred for 8 hours while keeping it at 0° C. and subsequently for 40 hours at room temperature, and then left quietly for 12 hours at room temperature. The upper-phase methylene chloride solution and the solid matter (mostly a reaction product of DCC) gathering at the upper part of an FC-72 phase (the lower phase) were removed. To the remaining solution (the lower phase), 50 parts by weight of methylene chloride was again added. The mixture obtained was stirred for 2 hours at room temperature, and thereafter left quietly for 12 hours at room temperature. Thereafter, the upper-phase methylene chloride solution and the solid matter gathering slightly at the upper part of the FC-72 phase were removed, and FC-72 of the remaining FC-72 solution was volatilized using an evaporator. Thereafter, FC-72 still remaining slightly was volatilized using a vacuum pump. Thus, 20 parts by weight of the desired compound 7 was obtained.

The compound 7 thus obtained showed substantially the same IR spectrum as that of the compound 1 except that the absorption due to the CO stretching vibration shifted from 1,710 $cm^{-1}$ to 1,810 $cm^{-1}$ and the absorption at 1,550 $cm^{-1}$ disappeared.

The 4'-(hydroxymethyl)benzo-15-crown-5 was synthesized in the following way.

First, 10 parts by weight of 4'-formylbenzo-15-crown-5 was suspended in 300 parts by weight of dried ethanol, then 4 parts by weight of sodium borohydride was added to the suspension, and the mixture obtained was stirred for 24 hours at room temperature. Next, 300 parts by weight of water was added to the reaction solution, and thereafter 50% acetic acid was added thereto little by little to neutralize it, followed by extraction with chloroform. The extract (organic layer) thus obtained was dried with sodium sulfate, and the chloroform was volatilized using an evaporator. Finally, the remaining residue was recrystallized with n-heptane to obtain 7 parts by weight of the 4'-(hydroxymethyl)benzo-15-crown-5.

SYNTHESIS EXAMPLE 8

A fluorine-containing compound represented by the following structural formula (28) (hereinafter "compound 8") was synthesized in the following manner. This compound is represented by the general formula (3) where $R^1$ is $R^3$, $Y^2$ is —$CH_2OCH_2$—, A is a benzene ring and m is 2.

(28)

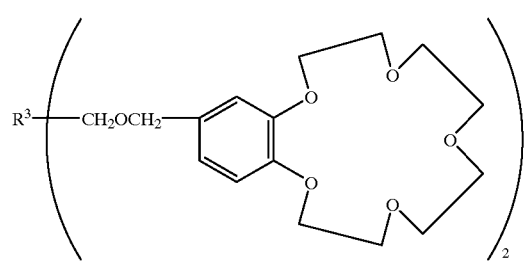

First, 1 part by weight of sodium hydride was added to 30 parts by weight of tetrahydrofuran (hereinafter "THF"), and the mixture obtained was thoroughly stirred to effect suspension. The reaction solution continued to be stirred until a quenching operation (described later) for terminating the reaction was completed. The reaction system was kept in an atmosphere of nitrogen until the quenching operation was completed.

Next, 4 parts by weight of 4'-(hydroxymethyl)benzo-15-crown-5 was dissolved in 30 parts by weight of THF, and the solution obtained was added dropwise to the sodium hydride solution in 2 hours with stirring. Subsequently, the mixture obtained was stirred for 2 hours, and thereafter a solution prepared by dissolving 20 parts by weight of the compound 4', obtained in the same manner as in Synthesis Example 4, in 100 parts by weight of FC-72, available from 3M, was added, followed by stirring for 48 hours.

Thereafter, 300 parts by weight of water was added to terminate the reaction. This is the quenching operation mentioned above. Next, the reaction solution was extracted with 100 parts by weight of FC-72. Thereafter, FC-72 of the FC-72 solution was volatilized using an evaporator, and FC-72 still remaining slightly was further volatilized using a vacuum pump. Thus, 18 parts by weight of the desired compound 8 was obtained.

The compound 8 exhibited substantially the same IR spectrum as that of the compound 7 except that the absorption due to the CO stretching vibration at 1,810 $cm^{-1}$ disappeared.

SYNTHESIS EXAMPLE 9

A fluorine-containing compound represented by the following structural formula (29) (hereinafter "compound 9")

was synthesized in the following manner. This compound is represented by the general formula (3) where $R^1$ is $R^3$, $Y^2$ is —CH$_3$OCOCH$_2$—, A is a benzene ring and m is 2.

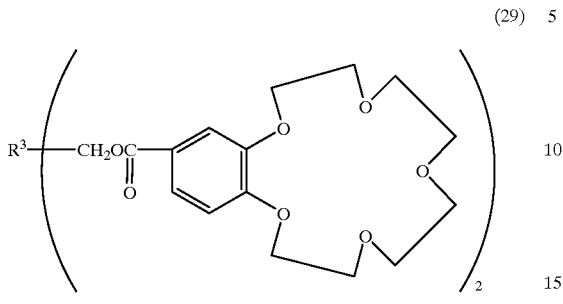

(29)

First, 4 parts by weight of 4'-(carboxy)benzo-15-crown-5 was dissolved in 30 parts by weight of methylene chloride, and 4 parts by weight of thionyl chloride was added thereto. The mixture obtained was stirred for 8 hours while refluxing it, followed by removal of the volatile component using an evaporator to obtain a 4'-(chloroformyl)benzo-15-crown-5 (hereinafter "compound 9'") in which the carboxyl group was converted to a chloroformyl group.

The compound 9' in its total weight (about 4 parts by weight) thus obtained was dissolved in 50 parts by weight of chloroform, and 2 parts by weight of pyridine was further added. To the mixture obtained, a solution prepared by dissolving 20 parts by weight of Fombrin Z-DOL (average molecular weight: 4,000), available from Ausimont Co., in 100 parts by weight of FC-75, available from 3M, was added. The mixture obtained was stirred for 48 hours while heating it to 60° C., thereafter cooled to room temperature and then left quietly for 12 hours, where the upper-phase chloroform phase and the solid matter gathering at the upper part of an FC-75 phase (the lower phase) were removed.

To the remaining lower-phase solution, 50 parts by weight of chloroform was again added. The mixture obtained was stirred for 2 hours at room temperature, and thereafter left quietly for 12 hours at room temperature, where the upper-phase chloroform solution and the solid matter gathering slightly at the upper part of the FC-75 phase were removed, and FC-75 of the remaining FC-75 solution was volatilized using an evaporator. Thereafter, FC-75 still remaining slightly was further volatilized using a vacuum pump. Thus, 20 parts by weight of the desired compound 9 was obtained.

The compound 9 thus obtained showed substantially the same IR spectrum as that of the compound 7.

The 4'-caroxybenzo-15-crown-5 was synthesized in the following way.

First, 17 parts by weight of silver nitrate was dissolved in 26 parts by weight of water, and a solution prepared by dissolving 8 parts by weight of sodium hydroxide in a mixed solvent of 25 parts by weight of water and 40 parts by weight of methanol was added thereto with stirring. To the mixture thus obtained, a suspension prepared by suspending 10 parts by weight of 4'-formylbenzo-15-crown-5 in 50 parts by weight of methanol was added slowly while keeping the liquid temperature at 45 to 50° C., and the reaction solution was stirred for 2 hours while keeping it at 45 to 50° C. Thereafter, the reaction solution was concentrated to about half the volume using an evaporator while keeping it at about 40° C.

The concentrated solution thus obtained was filtered with Celite (No. 535), available from Wako Pure Chemical Industries, Ltd. Thereafter, the filtrate was made acidic with 10% hydrochloric acid and extracted with 100 parts by weight of methylene chloride. The methylene chloride in the extract was volatilized using an evaporator, and the residue was recrystallized with ethyl acetate and n-heptane to obtain 8 parts by weight of the 4'-(carboxy)-benzo-15-crown-5.

SYNTHESIS EXAMPLE 10

A fluorine-containing compound represented by the following structural formula (30) (hereinafter "compound 10") was synthesized in the following manner. This compound is represented by the general formula (3) where $R^1$ is $R^3$, $Y^2$ is —CH$_3$OCOCH=CH—, A is a benzene ring and m is 2.

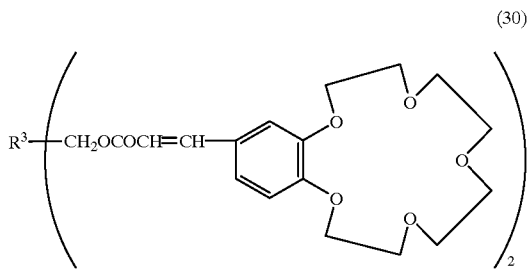

(30)

First, 10 parts by weight of 4'-formylbenzo-15-crown-5 was dissolved in 50 parts by weight of pyridine, and 7 parts by weight of malonic acid was added thereto. Thereafter, the mixture obtained was heated to 50° C. To this mixture, 1 part by weight of piperidine was added, and the mixture was stirred for 1 hour at 80° C. and subsequently stirred for 3 hours while refluxing it. Next, the reaction solution obtained was cooled to room temperature. Thereafter, it was poured into 500 parts by weight of chilled water, and made acidic with 10% hydrochloric acid, whereupon a solid became deposited. This solid was collected by filtration, washed with water, and then recrystallized with ethanol to obtain 7 parts by weight of the 4'-(2-carboxyvinyl)benzo-15-crown-5 (hereinafter "compound 10'").

Subsequently, 4 parts by weight of the compound 10' was dissolved in 20 parts by weight of chloroform, and 3 parts by weight of thionyl chloride was added. The mixture obtained was refluxed for 8 hours with stirring, and then cooled to room temperature. Thereafter, the reaction solution was evaporated to dryness using an evaporator to obtain 4 parts by weight of a compound in which the carboxyl group of the compound 10' was converted to a chloroformyl group, i.e., 4'-{2-(chloroformyl)vinyl}benzo-15-crown-5 (hereinafter "compound 10''").

Next, to a solution prepared by dissolving 20 parts by weight of Fombrin Z-DOL (average molecular weight: 4,000), available from Ausimont Co., in 100 parts by weight of FC-84, available from 3M, a solution prepared by dissolving 4 parts by weight of the compound 10" in 50 parts by weight of methylene chloride and 2 parts by weight of pyridine were added. The mixture obtained was stirred for 48 hours while heating it to 60° C., thereafter cooled to room temperature and then left quietly for 12 hours.

Next, from the reaction solution separated into two phases, the upper-phase chloroform solution and the solid matter gathering at the upper part of an FC-84 phase (the lower phase) were removed. To the remaining lower-phase solution, 50 parts by weight of chloroform was again added. The mixture obtained was stirred for 2 hours at room temperature, and thereafter left quietly for 12 hours at room temperature, where the upper-phase chloroform solution and the solid matter gathering slightly at the upper part of the FC-84 phase were again removed, and finally FC-84 of the remaining FC-84 solution was volatilized using an evaporator. Then, FC-84 still remaining slightly was further volatilized using a vacuum pump. Thus, 20 parts by weight of the desired compound 10 was obtained.

The compound 10 thus obtained showed substantially the same IR spectrum as that of the compound 7.

SYNTHESIS EXAMPLE 11

A fluorine-containing compound represented by the following structural formula (31) (hereinafter "compound 11") was synthesized in the following manner. This compound is represented by the general formula (3) where $R^1$ is $R^3$, $Y^2$ is —$CH_2OCOCH_2CH_2$—, A is a benzene ring and m is 2.

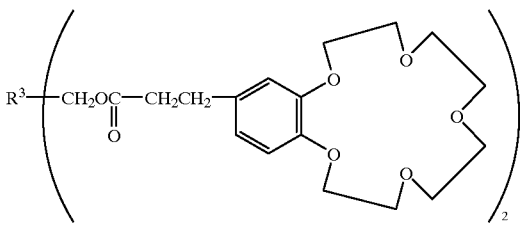
(31)

5 parts by weight of compound 10' synthesized in the same manner as in Synthesis Example 10 was placed into a thick-walled glass container, and 100 parts by weight of acetic acid was added thereto and dissolved with heating. Next, 0.2 part by weight of platinum(IV) oxide was added, and, after the inside of the container was displaced with hydrogen and the container was so plumbed that hydrogen was able to be fed in, the contents of the container were stirred vigorously for 3 hours. During the stirring, hydrogen was fed when the internal pressure of the container lowered.

At the time the internal pressure of the container came to little lower any longer, the pipe for feeding hydrogen was detached, and the reaction solution was filtered with Celite (No. 535), available from Wako Pure Chemical Industries, Ltd. From the filtrate obtained, the acetic acid was volatilized using an evaporator, and the acetic acid was further removed almost completely by azeotropic distillation with toluene. The residue thus obtained was recrystallized with n-hexane to obtain 4 parts by weight of the 4'-(2-carboxyethyl)benzo-15-crown-5 (hereinafter "compound 11'").

Next, the compound 11' in its total weight (4 parts by weight) thus obtained was dissolved in 20 parts by weight of chloroform, and 3 parts by weight of thionyl chloride was added. The mixture obtained was refluxed for 8 hours with stirring, and then the reaction solution was cooled to room temperature, followed by evaporation to dryness using an evaporator to obtain 4 parts by weight of a compound in which the carboxyl group of the compound 11' was converted to a chloroformyl group, i.e., 4'-{2-(chloroformyl)ethyl}benzo-15-crown-5 (hereinafter "compound 11'''").

Subsequently, a solution prepared by dissolving in 50 parts by weight of methylene chloride the compound 11" in its total weight (4 parts by weight) thus obtained and 2 parts by weight of pyridine were added to a solution prepared by dissolving 20 parts by weight of Fombrin Z-DOL (average molecular weight: 4,000), available from Ausimont Co., in 100 parts by weight of FC-84, available from 3M, was added. The mixture obtained was stirred for 48 hours while heating it to 60° C., and thereafter the reaction solution was cooled to room temperature and then left quietly for 12 hours.

Next, from the reaction solution separated into two phases, the upper-phase chloroform solution and the solid matter gathering at the upper part of an FC-84 phase (the lower phase) were removed. To the remaining lower-phase solution, 50 parts by weight of chloroform was again added. The mixture obtained was stirred for 2 hours at room temperature, and thereafter left quietly for 12 hours at room temperature. Thereafter, the upper-phase chloroform solution and the solid matter gathering slightly at the upper part of the FC-84 phase were removed, and FC-84 of the remaining FC-84 solution was volatilized using an evaporator. Then, FC-84 still remaining slightly was further volatilized by means of a vacuum pump. Thus, 20 parts by weight of the desired compound 11 was obtained.

The compound 11 thus obtained exhibited substantially the same IR spectrum as that of the compound 7.

SYNTHESIS EXAMPLE 12

A fluorine-containing compound represented by the following structural formula (32) (hereinafter "compound 12") was obtained in the same manner as in Synthesis Example 1 except that the 4'-aminobenzo-15-crown-5 was replaced with 7 parts by weight of 2-aminomethyl-15-crown-5. Yield was 20 parts by weight.

This compound is represented by the general formula (4) where $R^1$ is $R^3$, $Y^3$ is —$CONHCH_2$— and m is 2.

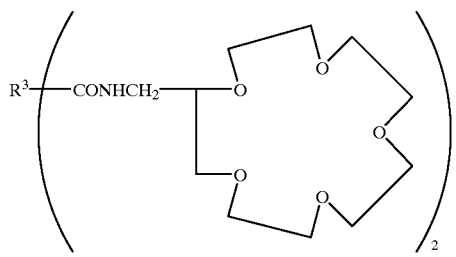
(32)

Figure 2:
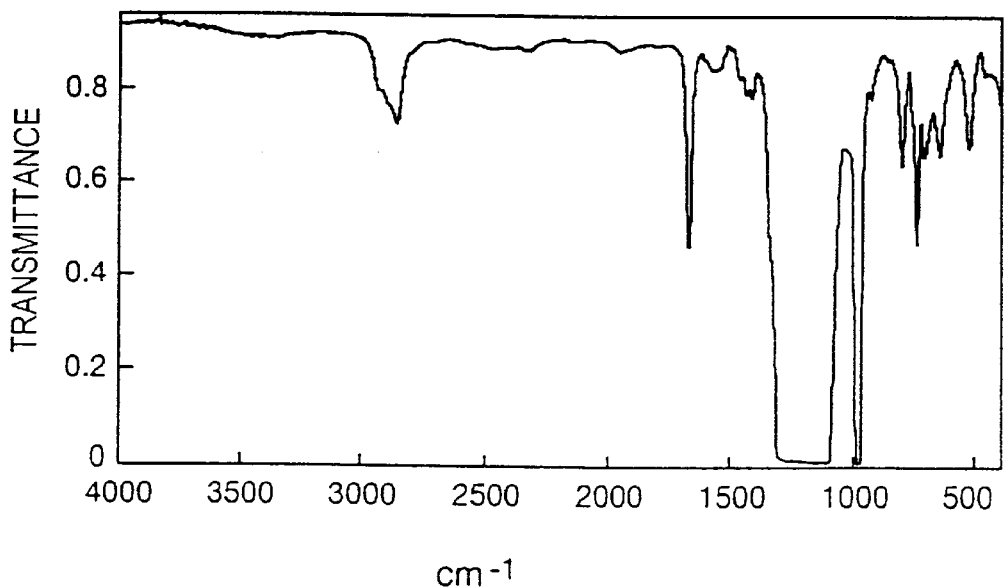
FIG. 2 shows an IR spectrum of compound 12.

An IR spectrum of the compound 12 thus obtained is shown in FIG. 2.

SYNTHESIS EXAMPLE 13

A fluorine-containing compound represented by the following structural formula (33) (hereinafter "compound 13") was obtained in the same manner as in Synthesis Example 1 except that the 4'-aminobenzo-15-crown-5 was replaced with 8 parts by weight of 2-aminomethyl-18-crown-6. Yield was 20 parts by weight.

This compound is represented by the general formula (4) where $R^1$ is $R^3$, $Y^3$ is —$CONHCH_2$— and m is 3.

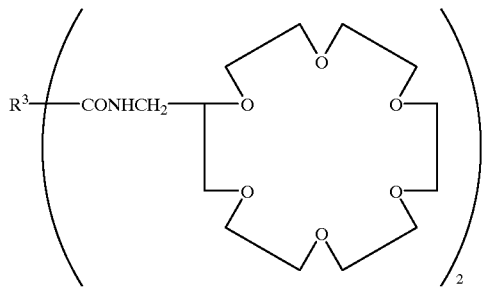
(33)

The compound 13 thus obtained showed substantially the same IR spectrum as that of the compound 12.

SYNTHESIS EXAMPLE 14

A fluorine-containing compound represented by the following structural formula (34) (hereinafter "compound 14")

was obtained in the same manner as in Synthesis Example 1 except that the 4'-aminobenzo-15-crown-5 was replaced with 7 parts by weight of 2-aminomethyl-12-crown-4. Yield was 19 parts by weight.

This compound is represented by the general formula (4) where $R^1$ is $R^3$, $Y^3$ is —CONHCH$_2$— and m is 1.

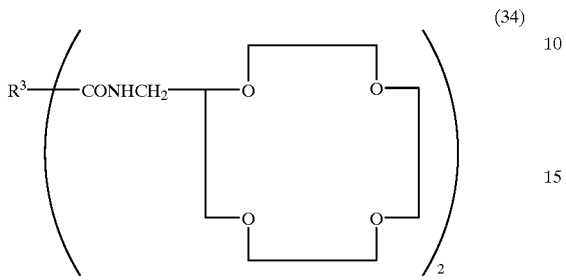
(34)

The compound 14 thus obtained exhibited substantially the same IR spectrum as that of the compound 12.

SYNTHESIS EXAMPLE 15

A fluorine-containing compound represented by the following structural formula (35) (hereinafter "compound 15") was obtained in the same manner as in Synthesis Example 1 except that the 4'-aminobenzo-15-crown-5 was replaced with 11 parts by weight of 2-aminomethyl-24-crown-8. Yield was 20 parts by weight. The compound 15 thus obtained exhibited substantially the same IR spectrum as that of the compound 12.

This compound is represented by the general formula (4) where $R^1$ is $R^3$, $Y^3$ is —CONHCH$_2$— and m is 5.

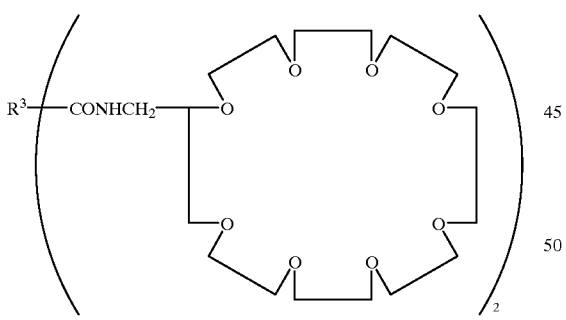
(35)

SYNTHESIS EXAMPLE 16

A fluorine-containing compound represented by the following structural formula (36) (hereinafter "compound 16") was obtained in the same manner as in Synthesis Example 8 except that the 4'-(hydroxymethyl)benzo-15-crown-5 was replaced with 4 parts by weight of 2-hydroxymethyl-15-crown-5. Yield was 17 parts by weight.

This compound is represented by the general formula (4) where $R^1$ is $R^3$, $Y^3$ is —CH$_2$OCH$_2$— and m is 2.

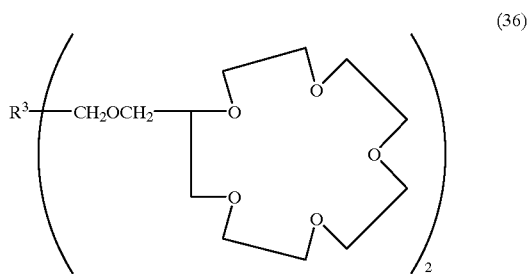
(36)

The compound 16 thus obtained showed substantially the same IR spectrum as that of the compound 1 except that the absorption at 1,710 cm$^{-1}$ due to the CO stretching vibration of the amide and absorption at 1,550 cm$^{-1}$ due to the NH bending vibration disappeared.

Figure 3:
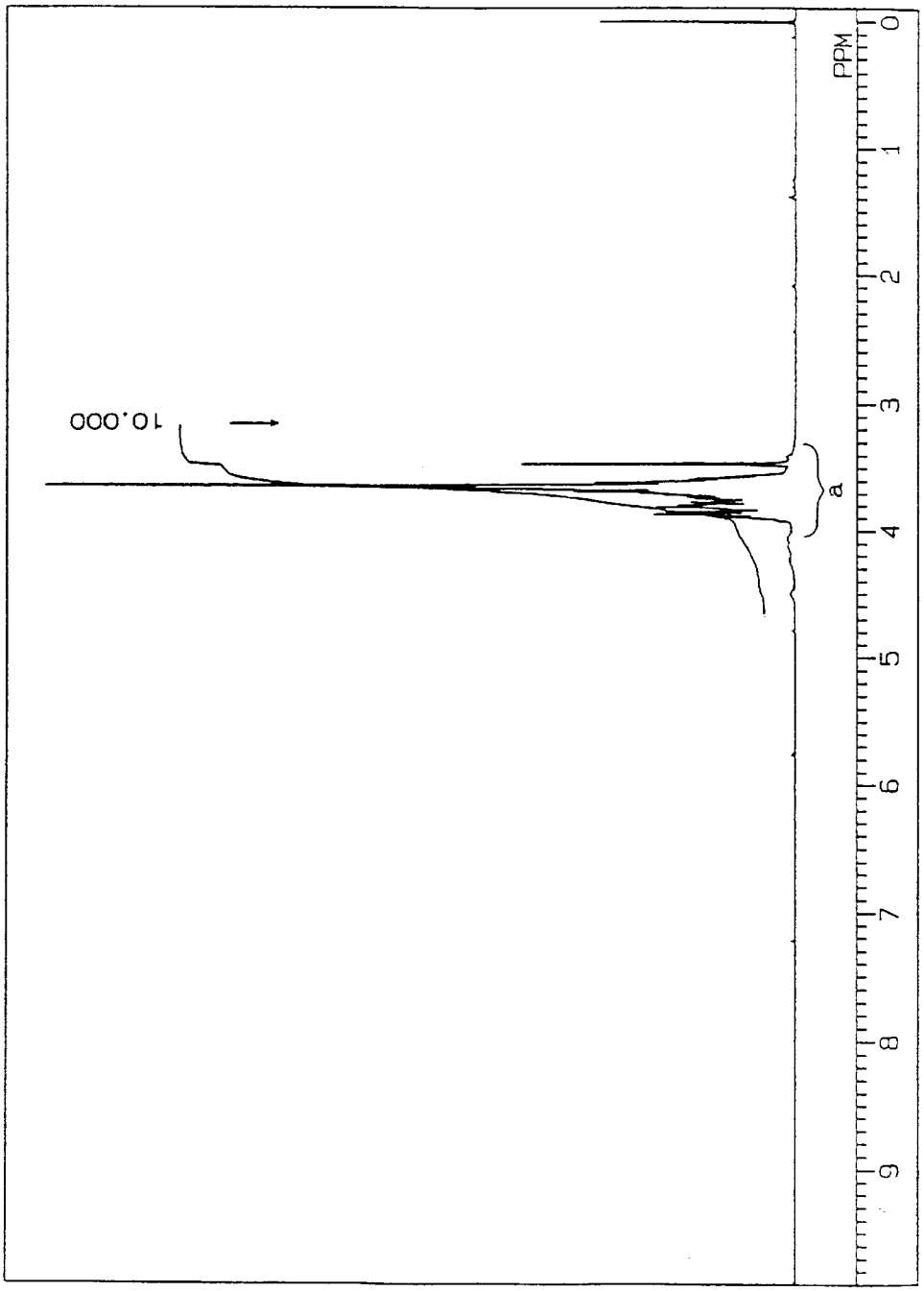
FIG. 3 is a $^1$H-NMR chart of compound 16.

A $^1$H-NMR chart of the compound 16 is shown in FIG. 3. Peaks a, due to the methylene group of the crown ether moiety, are seen at about 3.4 to 4.0 ppm.

Figure 4:
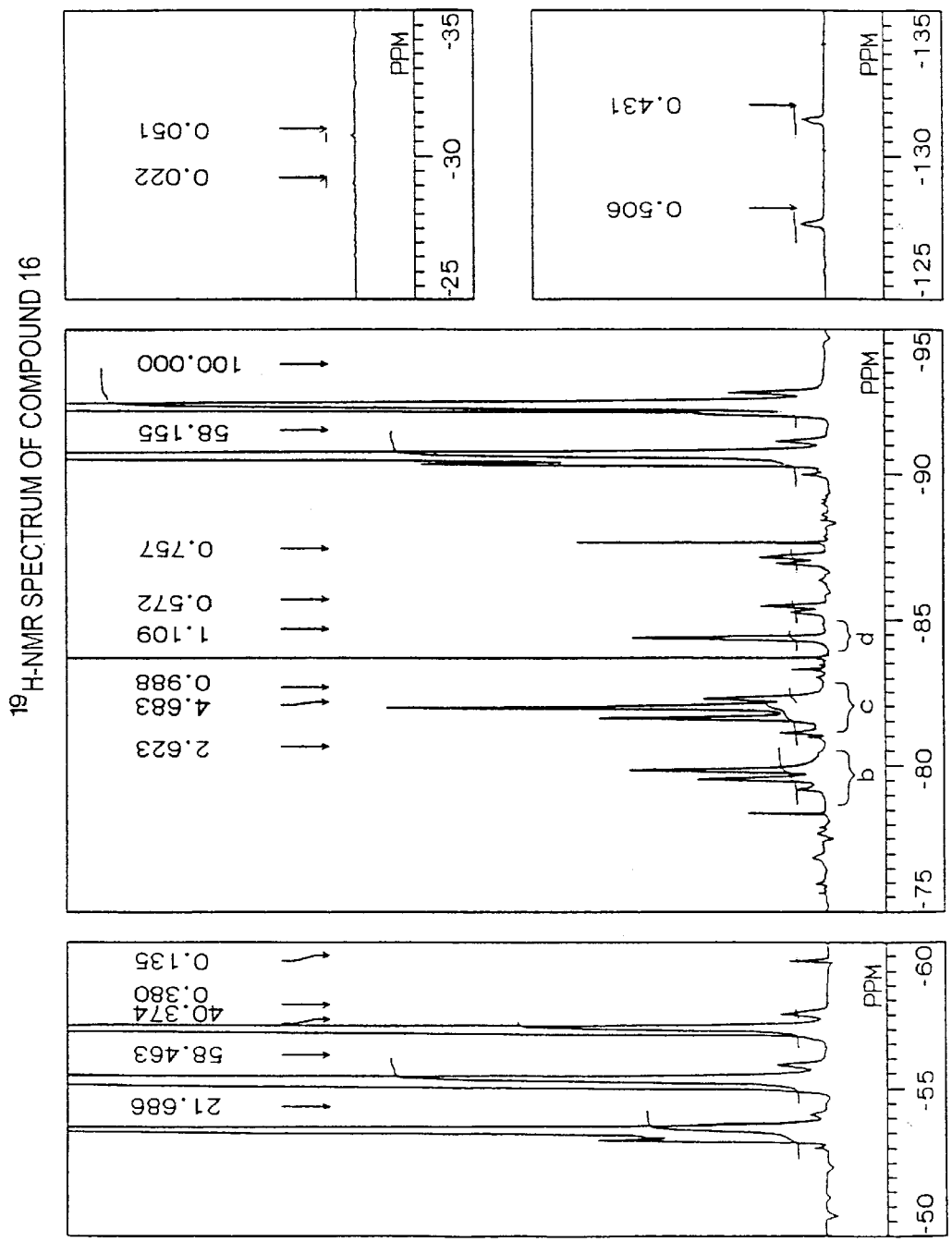
FIG. 4 is a $^{19}$F-NMR chart of compound 16.

A $^{19}$F-NMR chart of the compound 16 is shown in FIG. 4. Peaks, b and c, due to the CF$_2$ at the terminal of the perfluoropolyoxyethylene portion on its side bonded to $Y^3$ are seen at about −79 to −83 ppm.

These charts were obtained by taking measurements on a crude product in which the unreacted starting compound 4' remained. Thus, it is considered that peaks due to the methylene group of the compound 4' are mixedly present in the peaks a and c. It is also considered that the peak d at about −84.5 ppm in the $^{19}$F-NMR chart is due to the CF2 at the terminal of Fombrin Z-DOL, the starting material of the compound 4', on its side bonded to —CH$_3$OH.

The crude product on which the NMR measurement was made contained the starting material Fombrin Z-DOL and impurities in Fombrin Z-DOL, which were present in a compositional ratio of approximately compound 16:compound 4':impurities=74:20:6. As the impurities in Fombrin Z-DOL, those in which the terminal was OCF$_3$ in place of CH$_2$OH and those in which the terminal was CF$_2$Cl in place of CH$_3$OH were contained.

SYNTHESIS EXAMPLE 17

A fluorine-containing compound represented by the following structural formula (37) (hereinafter "compound 17") was synthesized in the following manner. This compound is represented by the general formula (5) where $R^1$ is $R^3$, $Y^4$ is —CO— and m is 2.

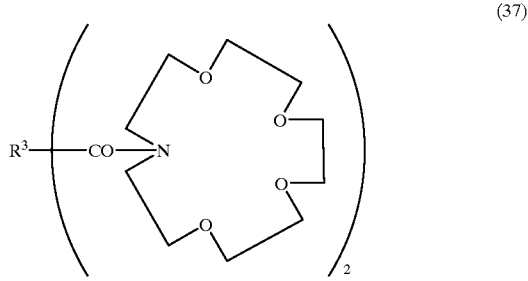
(37)

First, 20 parts by weight of Fombrin Z-DIAC (average molecular weight: 4,000), available from Ausimont Co., was dissolved in 100 parts by weight of FC-72, available from 3M, and 3 parts by weight of thionyl chloride was added thereto. The mixture obtained was ref luxed for 24 hours with stirring, and thereafter the reaction solution was cooled to room temperature, followed by evaporation to dryness using an evaporator to obtain a compound in which the carboxyl group of the starting material Z-DIAC was converted to a chloroformyl group (hereinafter "compound 17'").

Next, the compound 17' in its total weight thus obtained was dissolved in 100 parts by weight of FC-72. To the solution obtained, a solution prepared by dissolving 5 parts by weight of 1-aza-15-crown-5 and 3 parts by weight of pyridine in 50 parts by weight of methylene chloride was added. The mixture obtained was stirred for 1 hour at room temperature, and subsequently for 48 hours while ref luxing it.

The reaction solution thus obtained was cooled to room temperature, and thereafter left quietly for 12 hours. The upper phase methylene chloride solution a nd a solid depositing slightly were removed, and 20 parts by weight of a methanol solution of sodium hydroxide (5%) was added to the lower-phase FC-72 solution. The mixture obtained was stirred at room temperature, and thereafter further left quietly for 12 hours at room temperature.

Figure 5:
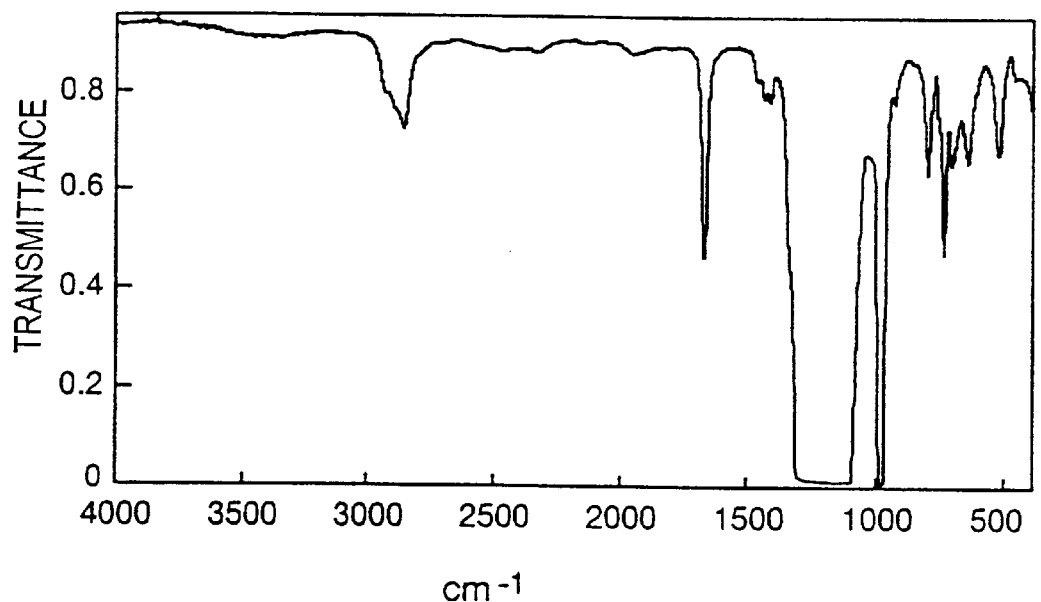
FIG. 5 shows an IR spectrum of compound 17.

Finally, from the reaction solution separated into two phases, the upper-phase methanol solution was removed, and FC-72 of the remaining FC-72 solution was volatilized. Thereafter, FC-72 still remaining slightly was further volatilized using a vacuum pump. Thus, 18 parts by weight of the desired compound 17 was obtained. An infrared (IR) spectrum of thus obtained compound 17 is shown in FIG. 5.

SYNTHESIS EXAMPLE 18

Figure 6:
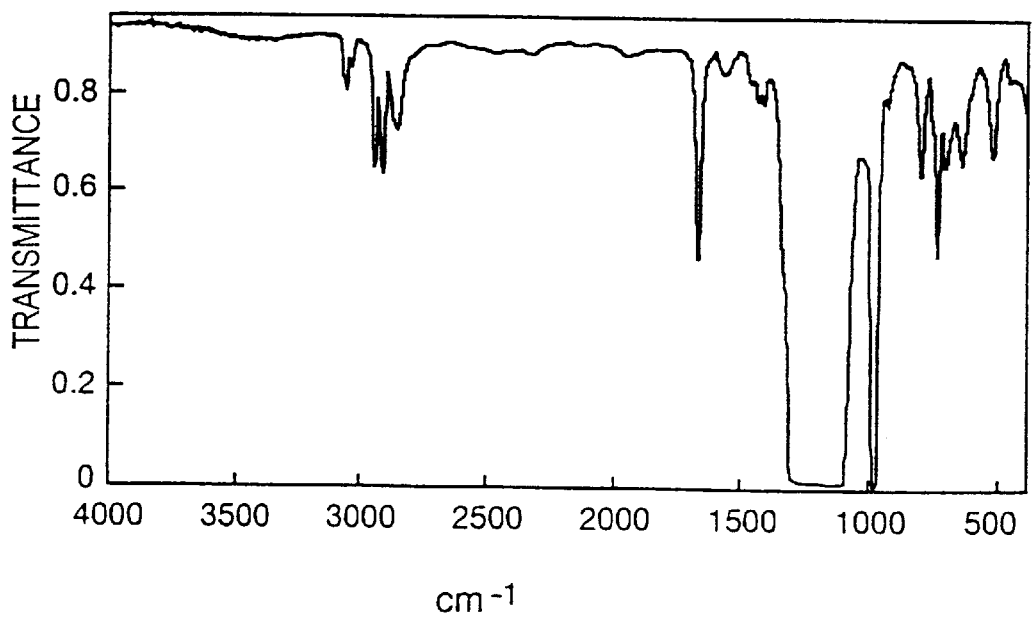
FIG. 6 shows an IR spectrum of compound 18.

A fluorine-containing compound represented by the following structural formula (38) (hereinafter "compound 18") was synthesized in the same manner as the compound 1 except that the 4'-aminobenzo-15-crown-5 was replaced with 8 parts by weight of 1,2-bis(2-methoxyethyloxy)-4-aminobenzene (hereinafter "compound 18'"). Yield was 20 parts by weight. An IR spectrum of thus obtained compound 18 is shown in FIG. 6.

This compound is represented by the general formula (7) where $R^1$ is $R^3$, $Y^6$ is —CONH—, A is a benzene ring, n is 1, $Z^1$ is —CH$_3$ and $Z^2$ is —O—.

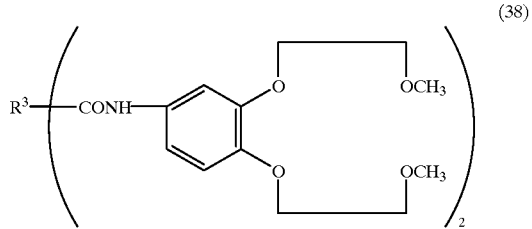

(38)

The compound 18" used as the starting material in the present Synthesis Example was synthesized in the following way.

First, 8 parts by weight of catechol was dissolved in 200 parts by weight of n-butanol, and thereafter the blowing of nitrogen gas with stirring was started. The nitrogen gas was blown in order to remove dissolved oxygen from the solution as completely as possible. The stirring and the blowing of nitrogen were continued until reflux stopped.

Next, 6 parts by weight of sodium hydroxide was dissolved in 30 parts by weight of water, and nitrogen gas was blown thereinto to prepare a solution from which the dissolved oxygen was removed as completely as possible. This solution was added to the above n-butanol solution, which was heated to 50° C. Thereafter, to this reaction mixture, 16 parts by weight of 2-chloroethyl methyl ether was added dropwise in 1 hour, and reflux was further continued for 24 hours.

The reaction solution thus obtained was cooled to room temperature, and thereafter evaporated to dryness using an evaporator. To the residue formed, 100 parts by weight of n-heptane was added to carry out reflux for 1 hour, and a supernatant liquid was collected while it was hot. This operation of extraction with n-heptane was repeated twice, and thereafter the extract was cooled to approximately –10° C., whereupon 1,2-bis(2-methoxyethyloxy)benzene (hereinafter "compound 18'") was deposited as a solid. Yield was 12 parts by weight.

Next, to a solution prepared by dissolving 12 parts by weight of the compound 18' in a mixed solvent of 200 parts by weight of chloroform and 150 parts by weight of acetic acid, 40 parts by weight of 70% nitric acid was added dropwise in 1 hour with stirring, further followed by stirring for 24 hours. Next, the reaction solution thus obtained was neutralized with a saturated aqueous sodium carbonate, and thereafter separated to obtain a chloroform phase. Finally, the chloroform solution obtained was dried with magnesium sulfate, and thereafter the chloroform was evaporated using an evaporator. The residue thus obtained was recrystallized with isobutanol to obtain a compound in which the benzene ring of the compound 18' was nitrated at the 4-position, i.e., the 1,2-bis(2-methoxyethyloxy)-4-nitrobenzene (11 parts by weight).

Subsequently, 150 parts by weight of N,N-dimethylformamide (hereinafter "DMF") was put into a thick-walled glass container, and 11 parts by weight of the 1,2-bis(2-methoxyethyloxy)-4-nitrobenzene thus obtained was added thereto and dissolved. To the resultant DMF solution, 1 part by weight of platinum (IV) oxide was added, and, after the inside of the container was displaced with hydrogen and the container was so plumbed that hydrogen was able to be fed in, the contents of the container were stirred vigorously for 3 hours. During the stirring, hydrogen was fed when the internal pressure of the container lowered.

At the time the internal pressure of the container came to little lower any longer, the pipe for feeding hydrogen was detached, and the reaction solution was filtered with Celite (No. 535), available from Wako Pure Chemical Industries, Ltd. Subsequently, from the filtrate obtained, the DMF was volatilized with an evaporator pressure-reduced by a vacuum pump. Thereafter, to the residue obtained, 150 parts by weight of 5% hydrochloric acid and 150 parts by weight of chloroform were added. The mixture obtained was thoroughly stirred and thereafter the aqueous phase was collected. The aqueous phase thus obtained was made basic with an aqueous 10% sodium hydroxide solution, followed by extraction with methylene chloride, and the methylene chloride was volatilized from the extract to obtain 8 parts by weight of the compound 18".

SYNTHESIS EXAMPLE 19

A fluorine-containing compound represented by the following structural formula (39) (hereinafter "compound 19") was synthesized in the same manner as the compound 18 except that the compound 18" was replaced with 18 parts by weight of 1,2-bis(3,6-dioxadocosyloxy)-4-aminobenzene (hereinafter "compound 19'"). Yield was 21 parts by weight.

This compound is represented by the general formula (7) where $R^1$ is $R^3$, $Y^6$ is —CONH—, A is a benzene ring, n is 2, $Z^1$ is —(CH$_2$)$_{15}$CH$_3$ and $Z^2$ is —O—.

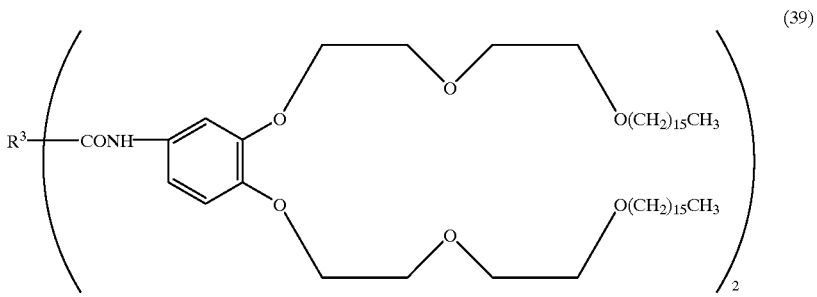

The compound 19 thus obtained exhibited substantially the same IR spectrum as that of the compound 18 except that the absorption at 3,000 to 2,800 cm$^{-1}$ due to the CH stretching vibration was greater.

The compound 19' used as the starting material in the present Synthesis Example is a compound which is a condensate of catechol with triethylene glycol mono-n-hexadecyl ether and in which an amino group was substituted for a hydrogen atom at the 4-position of the benzene ring. This compound 19' was synthesized in the same manner as the compound 18" except that the 2-chloroethyl methyl ether was replaced with 57 parts by weight of a compound in which chlorine was substituted for the hydroxyl group of the triethylene glycol mono-n-hexadecyl ether.

The compound in which chlorine was substituted for the hydroxyl group of triethylene glycol mono-n-hexadecyl ether was synthesized in the following way.

First, 80 parts by weight of triethylene glycol mono-n-hexadecyl ether was dissolved in a mixed solvent of 300 parts by weight of toluene and 50 parts by weight of pyridine. To the solution obtained, 50 parts by weight of thionyl chloride was added dropwise in about 3 hours with stirring while refluxing the mixture, which was subsequently refluxed for 24 hours, and thereafter the reaction solution was cooled to room temperature.

Subsequently, to the reaction solution 200 parts by weight of 5% hydrochloric acid was added dropwise slowly (in about 1 hour), and thereafter the toluene phase was collected. The toluene solution thus obtained was washed thoroughly with an aqueous 10% sodium chloride solution until the washing turned neutral, and thereafter the toluene was volatilized using an evaporator. Finally, the remaining liquid was distilled under reduced pressure to obtain a compound in which the hydroxyl group of triethylene glycol mono-n-hexadecyl ether was chlorinated, i.e., 1-chloro-3,6-dioxadocosane.

SYNTHESIS EXAMPLE 20

A fluorine-containing compound represented by the following structural formula (40) (hereinafter "compound 20") was synthesized in the same manner as the compound 18 except that the compound 18" was replaced with 32 parts by weight of 1,2-bis(3,6,9,12,15,18,21,24-octaoxatetracontyloxy)-4-aminobenzene (hereinafter "compound 20"). Yield was 22 parts by weight.

This compound is represented by the general formula (7) where $R^1$ is $R^3$, $Y^6$ is —CONH—, A is a benzene ring, n is 8, $Z^1$ is —(CH$_2$)$_{15}$CH$_3$ and $Z^2$ is —O—.

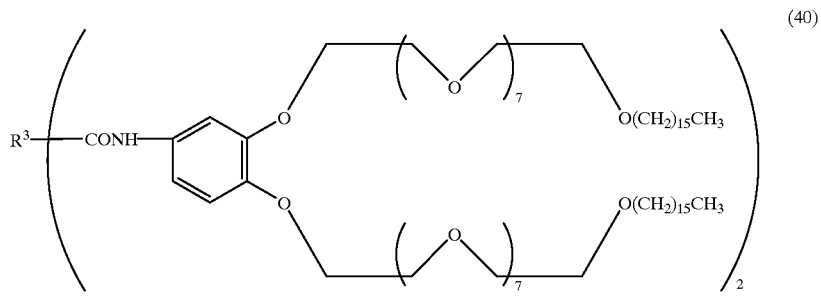

The compound 20 thus obtained showed substantially the same IR spectrum as that of the compound 18 except that the absorption at 3,000 to 2,800 cm$^{-1}$ due to the CH stretching vibration was greater.

The compound 20' used as the starting material in the present Synthesis Example was synthesized in the same manner as the compound 19' except that the triethylene glycol mono-n-hexadecyl ether was replaced with 135 parts by weight of octaethylene glycol mono-n-hexadecyl ether.

SYNTHESIS EXAMPLE 21

A fluorine-containing compound represented by the following structural formula (41) (hereinafter "compound 21") was synthesized in the same manner as the compound 18 except that the compound 18" was replaced with 18 parts by weight of 1,2-bis(3,6-dioxaoctadecyloxy)-4-aminobenzene (hereinafter "compound 21'"). Yield was 21 parts by weight.

This compound is represented by the general formula (7) where $R^1$ is $R^3$, $Y^6$ is —CONH—, A is a benzene ring, n is 2, $Z^1$ is —(CH$_2$)$_{11}$CH$_3$ and $Z^2$ is —O—.

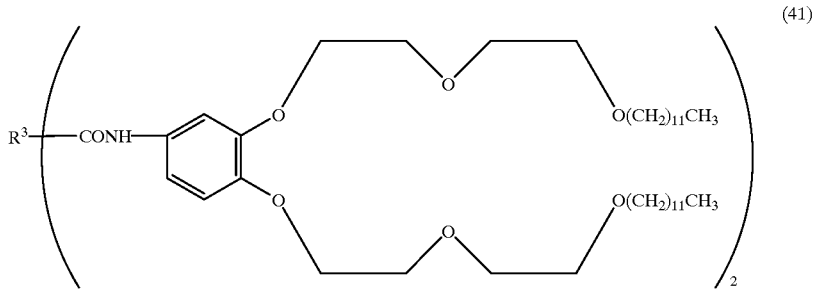

(41)

The compound 21 thus obtained showed substantially the same IR spectrum as that of the compound 18 except that the absorption at 3,000 to 2,800 cm$^{-1}$ due to the CH stretching vibration was greater.

The compound 21' used as the starting material in the present Synthesis Example was synthesized in the same manner as the compound 19' except that the triethylene glycol mono-n-hexadecyl ether was replaced with 57 parts by weight of triethylene glycol mono-n-dodecyl ether.

SYNTHESIS EXAMPLE 22

A fluorine-containing compound represented by the following structural formula (42) (hereinafter "compound 22") was synthesized in the same manner as the compound 18 except that the compound 18" was replaced with 32 parts by weight of 1,2-bis(3,6,9,12,15,18,21,24-octaoxahexatriacontyloxy)-4-aminobenzene (hereinafter "compound 22'"). Yield was 22 parts by weight.

This compound is represented by the general formula (7) where $R^1$ is $R^3$, $Y^6$ is —CONH—, A is a benzene ring, n is 8, $Z^1$ is —(CH$_2$)$_{11}$CH$_3$ and $Z^2$ is —O—.

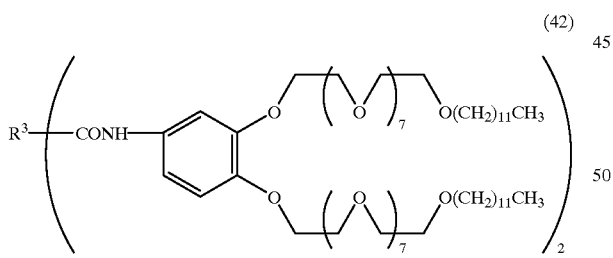

(42)

The compound 22 thus obtained exhibited substantially the same IR spectrum as that of the compound 18 except that the absorption at 3,000 to 2,800 cm$^{-1}$ due to the CH stretching vibration was greater.

The compound 22' used as the starting material in the present Synthesis Example was synthesized in the same manner as the compound 19' except that the triethylene glycol mono-n-hexadecyl ether was replaced with 135 parts by weight of octaethylene glycol mono-n-dodecyl ether.

SYNTHESIS EXAMPLE 23

A fluorine-containing compound represented by the following structural formula (43) (hereinafter "compound 23") was synthesized in the same manner as in Synthesis Example 1 except that Z-DIAC was replaced with 35 parts by weight of Demnum SH (average molecular weight: 3,500), available from Daikin Industries, Ltd. Yield was 35 parts by weight. The compound 23 thus obtained exhibited substantially the same IR spectrum as that of the compound 1.

This compound is represented by the general formula (10) where $R^2$ is $R^4$, $Y^2$ is —CONH—, A is a benzene ring and n is 2. Here, $R^4$ is CF$_3$CF$_2$CF$_2$O(CF$_2$CF$_2$CF$_2$O)$_\alpha$—; $\alpha$ is a positive number.

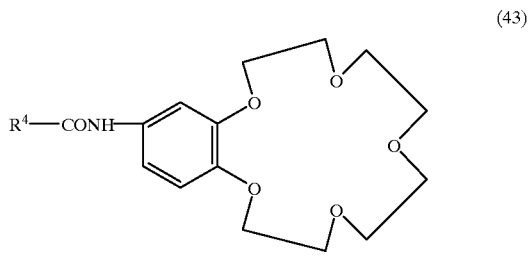

(43)

SYNTHESIS EXAMPLE 24

A fluorine-containing compound represented by the following structural formula (44) (hereinafter "compound 24") was synthesized in the same manner as in Synthesis Example 1 except that Z-DIAC was replaced with 25 parts by weight of Krytox 157FSL (average molecular weight: 2,400), available from Du Pont. Yield was 25 parts by weight. The compound 24 thus obtained exhibited substantially the same IR spectrum as that of the compound 1.

This compound is represented by the general formula (10) where $R^2$ is $R^4$, $Y^2$ is —CONH—, A is a benzene ring and m is 2. Here, $R^5$ is CF$_3$CF$_2$CF$_2$O{CF(CF$_3$)CF$_3$O)$_\alpha$—; $\alpha$ is a positive number.

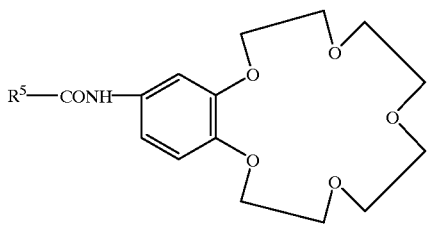

(44)

SYNTHESIS EXAMPLE 25

A fluorine-containing compound represented by the following structural formula (45) (hereinafter "compound 25") was synthesized in the same manner as in Synthesis Example 23 except that the 4'-aminobenzo-15-crown-5 was replaced with 7 parts by weight of 2-(aminomethyl)-15-crown-5. Yield was 34 parts by weight. The compound 25 thus obtained showed substantially the same IR spectrum as that of the compound 12.

This compound is represented by the general formula (11) where $R^2$ is $R^4$, $Y^3$ is —CONHCH$_2$— and m is 2.

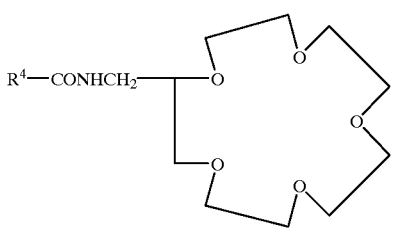

(45)

SYNTHESIS EXAMPLE 26

A fluorine-containing compound represented by the following structural formula (46) (hereinafter "compound 26") was synthesized in the same manner as in Synthesis Example 24 except that the 4'-aminobenzo-15-crown-5 was replaced with 7 parts by weight of 2-(aminomethyl)-15-crown-5. Yield was 24 parts by weight. The compound 26 thus obtained exhibited substantially the same IR spectrum as that of the compound 12.

This compound is represented by the general formula (11) where $R^2$ is $R^4$, $Y^3$ is —CONHCH$_2$— and m is 2.

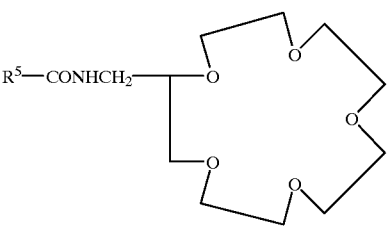

(46)

SYNTHESIS EXAMPLE 27

A fluorine-containing compound represented by the following structural formula (47) (hereinafter "compound 27") was synthesized in the same manner as in Synthesis Example 24 except that the 4'-aminobenzo-15-crown-5 was replaced with 2 parts by weight of 4,4¹-di(aminobenzo)-18-crown-6. Also, between the second-time operation to remove methylene chloride and the operation to volatilize 3M's FC-72 using an evaporator, an operation was added in which 10 parts by weight of a methanol solution of 5% sodium hydroxide was added to the reaction solution, the mixture obtained was stirred at room temperature and subsequently left quietly for 12 hours at room temperature and the upper-phase methanol solution was removed.

This compound is represented by the general formula (13) where $R^2$'s are each $R^5$, $Y^7$'s are each —CONH—, A's are each a benzene ring and p's are each 1.

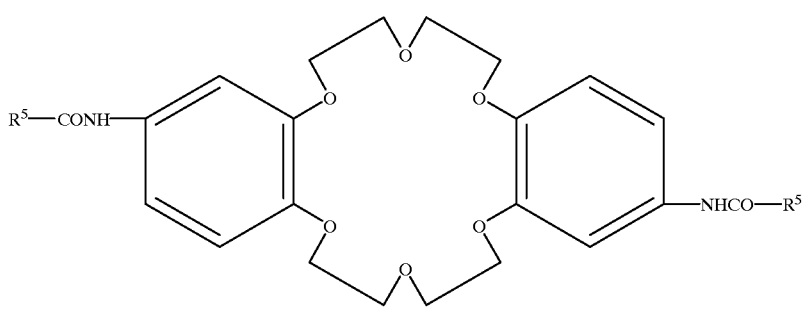

(47)

Figure 7:
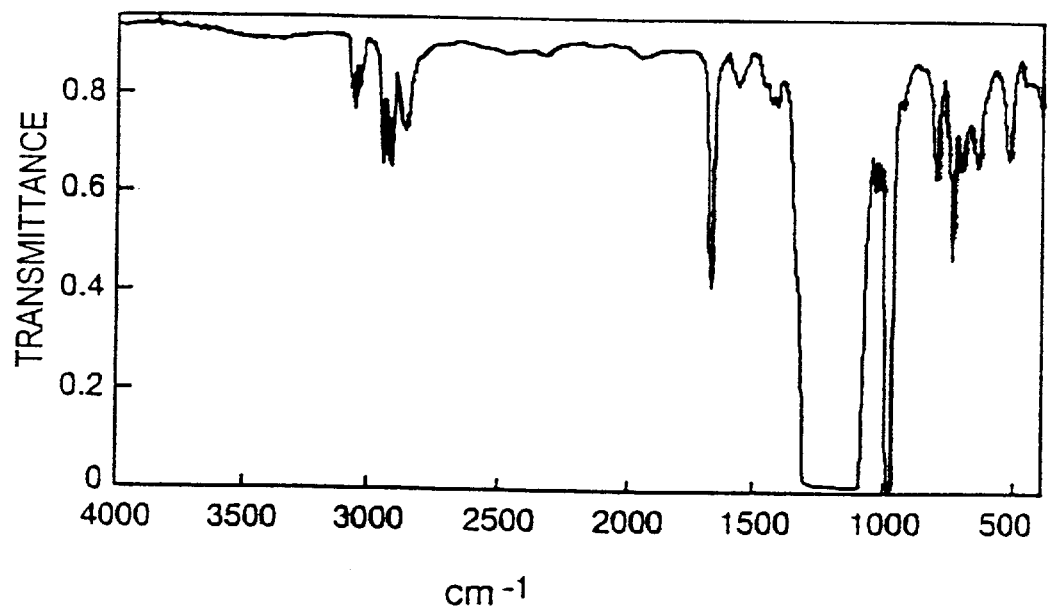
FIG. 7 shows an IR spectrum of compound 27.

The compound 27 was in a yield of 15 parts by weight. An IR spectrum of the compound 27 is shown in FIG. 7.

SYNTHESIS EXAMPLE 28

A fluorine-containing compound represented by the following structural formula (48) (hereinafter "compound 28") was synthesized in the same manner as in Synthesis Example 27 except that the 4,4'-di(aminobenzo)-18-crown-6 (2 parts by weight) was replaced with 2 parts by weight of 4,4'-di(aminobenzo)-24-crown-8. Yield was 10 parts by weight. The compound 28 thus obtained exhibited substantially the same IR spectrum as that of the compound 27.

This compound is represented by the general formula (13) where $R^2$'s are each $R^5$, $Y^7$'s are each —CONH— and p's are each 2.

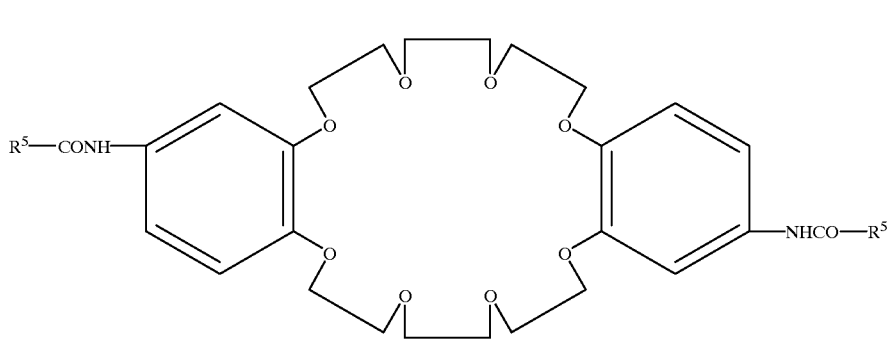

(48)

The 4,4'-di(aminobenzo)-24-crown-8 was obtained by nitrating dibenzo-24-crown-8 followed by reduction. This was operated in substantially the same manner as the process of synthesizing 4,4'-di(aminobenzo)-18-crown-6, disclosed in W. M. Feigenbaum and R. H. Michel, "Journal of Polymer Science", p.817, Vol. 9, Part A-1 (1970).

SYNTHESIS EXAMPLE 29

A fluorine-containing compound represented by the following structural formula (49) (hereinafter "compound 29") was synthesized in the following manner. This compound is represented by the general formula (13) where $R^2$'s are each changed for $R^5$, $Y^7$'s are each —CH$_2$OCO—, A's are each a benzene ring and p's are each 1.

First, 25 parts by weight of Krytox 157FSL, available from Du Pont, was dissolved in 200 parts by weight of FC-72, available from 3M, and 3 parts by weight of thionyl chloride was added thereto. The mixture obtained was refluxed for 24 hours with stirring, and thereafter the reaction solution was cooled to room temperature, followed by evaporation to dryness using an evaporator to obtain a compound in which the carboxyl group of Krytox 157FSL was converted to a chloroformyl group (hereinafter "compound 29'").

Next, the compound 29' in its total weight thus obtained was dissolved in 200 parts by weight of FC-72. To the solution obtained, a solution prepared by dissolving 2 parts by weight of 4,4'-di(hydroxymethyl)benzo-18-crown-6 and 1 part by weight of pyridine in 20 parts by weight of methylene chloride was added. The mixture obtained was stirred for 1 hour at room temperature, and subsequently allowed to react for 48 hours while refluxing it. The reaction solution thus obtained was cooled to room temperature, and thereafter left quietly for 12 hours.

From the reaction solution separated into two phases, the upper-phase methylene chloride solution and a solid depositing slightly were removed, and 200 parts by weight of methanol was added to the lower-phase FC-72 solution. The mixture obtained was stirred at room temperature, and thereafter subsequently left quietly for 12 hours at room temperature. Then, the upper-phase methanol solution was removed, and FC-72 of the remaining FC-72 solution was volatilized. Thereafter, FC-72 still remaining slightly was further volatilized using a vacuum pump. Thus, 10 parts by weight of the desired compound 29 was obtained.

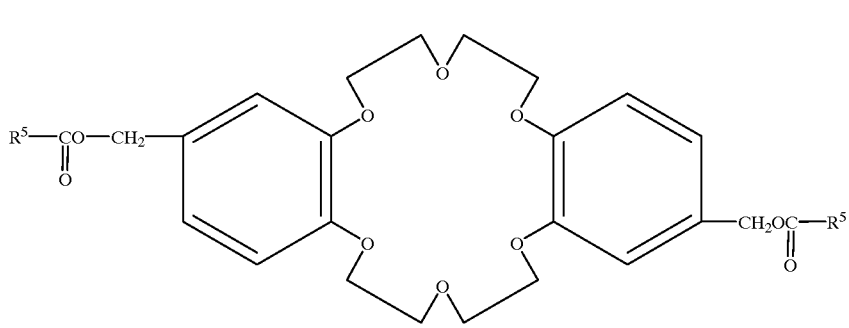

(49)

The compound 29 thus obtained exhibited substantially the same IR spectrum as that of the compound 27 except that the absorption due to the CO stretching vibration shifted from 1,710 cm$^{-1}$ to 1,810 cm$^{-1}$ and the absorption at 1,550 cm$^{-1}$ disappeared.

SYNTHESIS EXAMPLE 30

A fluorine-containing compound represented by the following structural formula (50) (hereinafter "compound 30") was synthesized in the same manner as in Synthesis Example 17 except that Fombrin Z-DIAC was replaced with 35 parts by weight of Demnum SH (average molecular weight: 3,500), available from Daikin Industries, Ltd., and FC-72 was replaced with 100 parts by weight of FC-75, available from 3M. Yield was 30 parts by weight.

This compound is represented by the general formula (12) where $R^2$ is $R^4$, $Y^4$ is —CO— and m is 2.

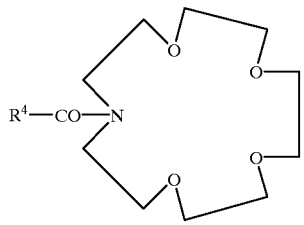

(50)

The compound 30 thus obtained exhibited substantially the same IR spectrum as that of the compound 17.

SYNTHESIS EXAMPLE 31

A fluorine-containing compound represented by the following structural formula (51) (hereinafter "compound 31") was synthesized in the same manner as in Synthesis Example 17 except that Fombrin Z-DIAC was replaced with 25 parts by weight of Krytox 157FSL (average molecular weight: 2,400), available from Du Pont, and FC-72 was replaced with 100 parts by weight of FC-75, available from 3M. Yield was 21 parts by weight.

This compound is represented by the general formula (12) where $R^2$ is $R^5$, $Y^4$ is —CO— and m is 2.

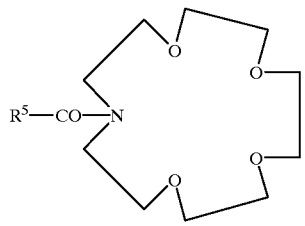

(51)

The compound 31 thus obtained showed substantially the same IR spectrum as that of the compound 17.

SYNTHESIS EXAMPLE 32

A fluorine-containing compound represented by the following structural formula (52) (hereinafter "compound 32") was synthesized in the same manner as in Synthesis Example 31 except that the 1-aza-15-crown-5 was replaced with 5 parts by weight of 1-aza-18-crown-6. Yield was 21 parts by weight.

This compound is represented by the general formula (12) where $R^2$ is $R^5$, $Y^4$ is —CO— and m is 3.

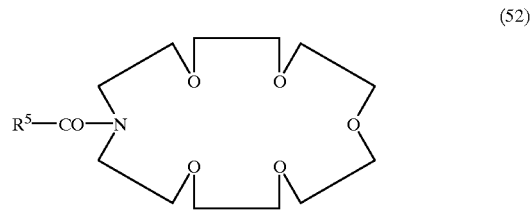

(52)

The compound 32 thus obtained exhibited substantially the same IR spectrum as that of the compound 17.

SYNTHESIS EXAMPLE 33

A fluorine-containing compound represented by the following structural formula (53) (hereinafter "compound 33") was synthesized in the same manner as in Synthesis Example 31 except that the 1-aza-15-crown-5 was replaced with 6 parts by weight of 1-aza-24-crown-4. Yield was 21 parts by weight.

This compound is represented by the general formula (12) where $R^2$ is $R^5$, $Y^4$ is —CO— and m is 5.

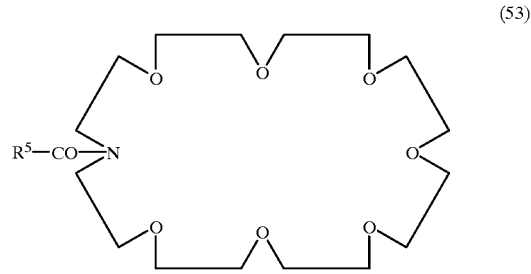

(53)

The compound 33 thus obtained exhibited substantially the same IR spectrum as that of the compound 17.

SYNTHESIS EXAMPLE 34

A fluorine-containing compound represented by the following structural formula (54) (hereinafter "compound 34") was synthesized in the same manner as in Synthesis Example 31 except that the 1-aza-15-crown-5 was replaced with 3 parts by weight of 1-aza-12-crown-4. Yield was 20 parts by weight.

This compound is represented by the general formula (12) where $R^2$ is $R^5$, $Y^4$ is —CO— and m is 1.

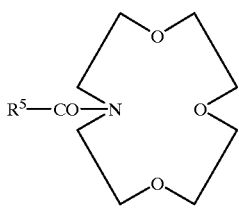

(54)

The compound 34 thus obtained exhibited substantially the same IR spectrum as that of the compound 17.

SYNTHESIS EXAMPLE 35

A fluorine-containing compound represented by the following structural formula (55) (hereinafter "compound 35") was synthesized in the same manner as in Synthesis Example 31 except that the 1-aza-15-crown-5 was replaced with 1 part by weight of 1,7,10,16-tetraoxa-4,13-diazacyclooctadecane. Also, before 20 parts by weight of the methanol solution of 5% sodium hydroxide was added, an operation was additionally carried out in which 20 parts by weight of an aqueous 10% sodium hydroxide solution was added to the lower-phase FC-72 solution, the mixture obtained was stirred for 1 hour at room temperature and thereafter left quietly for 24 hours and the upper-phase aqueous sodium hydroxide solution was removed. The compound 35 was in a yield of 15 parts by weight.

This compound is represented by the general formula (15) where $R^2$'s are each $R^5$, $Y^8$'s are each —CO— and q's are each 2.

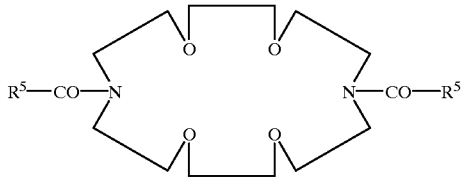

(55)

Figure 8:
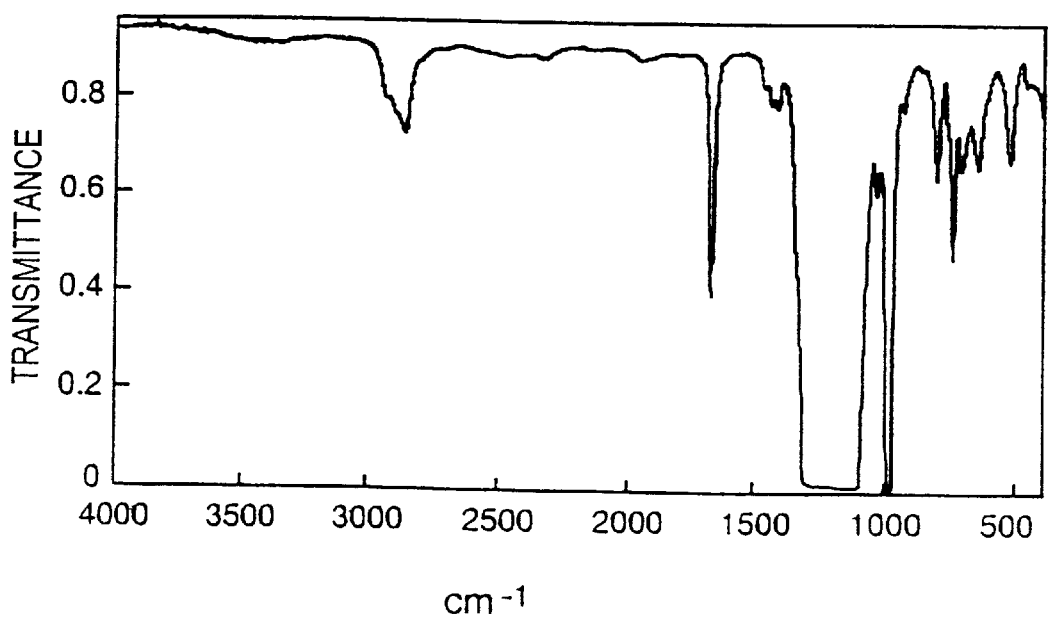
FIG. 8 shows an IR spectrum of compound 35.

An IR spectrum of the compound 35 is shown in FIG. 8.

SYNTHESIS EXAMPLE 36

A fluorine-containing compound represented by the following structural formula (56) (hereinafter "compound 36") was synthesized in the same manner as in Synthesis Example 35 except that the 1,7,10,16-tetraoxa-4,13-diazacyclooctadecane was replaced with 1 part by weight of 1,7,13-trioxa-4,10,16-triazacyclooctadecane. Yield was 14 parts by weight.

This compound is represented by the general formula (16) where $R^2$'s are each changed for $R^5$ and $Y^8$'s are each —CO—.

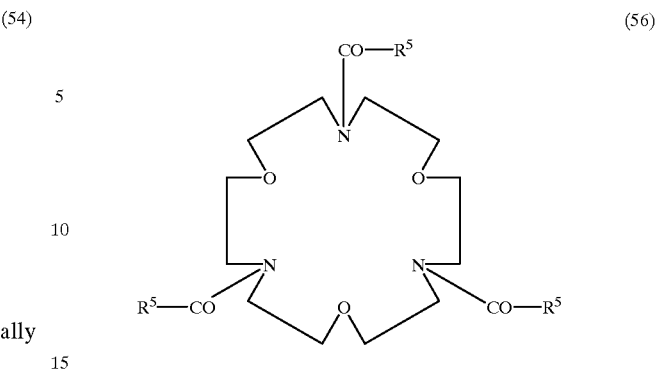

(56)

The compound 36 thus obtained showed substantially the same IR spectrum as that of the compound 35.

The 1,7,13-trioxa-4,10,16-triazacyclooctadecane was synthesized in substantially the same manner as the process disclosed in S. A. G. Hogberg and D. J. Cram, "Journal of the Organic Chemistry", p.151, Vol. 40, (1975).

SYNTHESIS EXAMPLE 37

A fluorine-containing compound represented by the following structural formula (57) (hereinafter "compound 37") was synthesized in the same manner as in Synthesis Example 18 except that Z-DIAC was replaced with 35 parts by weight of Demnum SH (average molecular weight: 3,500), available from Daikin Industries, Ltd. Yield was 20 parts by weight. The compound 37 thus obtained exhibited substantially the same IR spectrum as that of the compound 18.

This compound is represented by the general formula (18) where $R^2$ is $R^4$, $Y^6$ is —CONH—, A is a benzene ring, $Z^1$ is a methyl group and $Z^2$ is —O—.

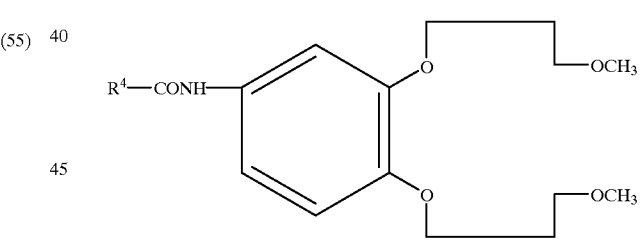

(57)

EXAMPLE 1

In the present Example, the compounds 1 to 37 were examined for their effect as surface modifiers in the following way.

First, silicon wafers of 2.5 inches in diameter were immersed for 1 minute in FC-72 solutions in which the respective fluorine-containing compounds were dissolved in a concentration of 0.1% by weight. Thereafter, these were drawn up at a rate of 1 mm/second, and were left for 2 hours at room temperature to volatilize the solvent. Thus, films of the fluorine-containing compounds were formed on the wafer surfaces to obtain samples.

Next, contact angles to water on the surfaces of the samples were examined. The results are shown in Table 1. Incidentally, before the films of fluorine-containing compounds were formed, the contact angle of each wafer surface was 26°. As can be seen from this Table 1, the compounds 1 to 37 are all effective as surface modifiers which can improve the water repellency of the surfaces to be treated.

TABLE 1

| Compound coated | 1 | 2 | 3 | 4 | 5 | 6 | 7 | 8 |
|---|---|---|---|---|---|---|---|---|
| Contact angle (degrees) | 95 | 100 | 90 | 95 | 95 | 95 | 95 | 95 |
| Compound coated | 9 | 10 | 11 | 12 | 13 | 14 | 15 | 16 |
| Contact angle (degrees) | 95 | 100 | 100 | 90 | 90 | 90 | 90 | 90 |
| Compound coated | 17 | 18 | 19 | 20 | 21 | 22 | 23 | 24 |
| Contact angle (degrees) | 90 | 100 | 95 | 100 | 95 | 100 | 100 | 90 |
| Compound coated | 25 | 26 | 27 | 28 | 29 | 30 | 31 | 32 |
| Contact angle (degrees) | 95 | 90 | 100 | 100 | 100 | 95 | 90 | 90 |
| Compound coated | 33 | 34 | 35 | 36 | 37 | | | |
| Contact angle (degrees) | 90 | 95 | 100 | 100 | 100 | | | |

EXAMPLE 2

In the present Example, the compounds 1 to 37 were examined for their scattering properties in the following way.

First, on the samples prepared in Example 1, their IR spectra were measured. Next, the samples were kept in a 120° C. thermostatic chamber for 10 hours, and thereafter their IR spectra were again measured to estimate the residue (residual quantity) of each fluorine-containing compound on the sample surface on the basis of a change of intensity of the absorption due to CF stretching vibration in the IR spectrum. The results are shown in Table 2.

In Table 2, "residue proportion" indicates a value obtained by dividing an absorption maximum after the sample has been left in the 120° C. thermostatic chamber for 10 hours by an absorption maximum before the sample is put in the thermostatic chamber. It means that, the greater the value is, the lower scattering properties the sample has. As can be seen from Table 2, the compounds 1 to 37 are all lubricants having low scattering properties and a high stability.

TABLE 2

| Compound coated | 1 | 2 | 3 | 4 | 5 | 6 | 7 | 8 |
|---|---|---|---|---|---|---|---|---|
| Residue proportion (%) | 74 | 75 | 74 | 76 | 77 | 75 | 73 | 71 |
| Compound coated | 9 | 10 | 11 | 12 | 13 | 14 | 15 | 16 |
| Residue proportion (%) | 73 | 75 | 76 | 71 | 71 | 72 | 70 | 70 |
| Compound coated | 17 | 18 | 19 | 20 | 21 | 22 | 23 | 24 |
| Residue proportion (%) | 70 | 74 | 82 | 84 | 80 | 82 | 73 | 71 |
| Compound coated | 25 | 26 | 27 | 28 | 29 | 30 | 31 | 32 |
| Residue proportion (%) | 70 | 69 | 78 | 77 | 78 | 70 | 69 | 70 |
| Compound coated | 33 | 34 | 35 | 36 | 37 | | | |
| Residue proportion (%) | 69 | 70 | 74 | 76 | 74 | | | |

COMPARATIVE EXAMPLE 1

For comparison, using AM2001, available from Ausimont Co., its scattering properties were determined in the same manner as in Example 2. As a result, its residue proportion was 58%. As can be seen from this result, the compounds 1 to 37 of the present invention all have lower scattering properties than the conventional lubricant.

AM2001 is a fluorine-containing compound having an average molecular weight of about 2,000, commonly used as a lubricant for magnetic disks, and has a structure wherein piperonyl groups are bonded to both terminals of a perfluoropolyoxyalkylene chain.

EXAMPLE 3

Figure 9:
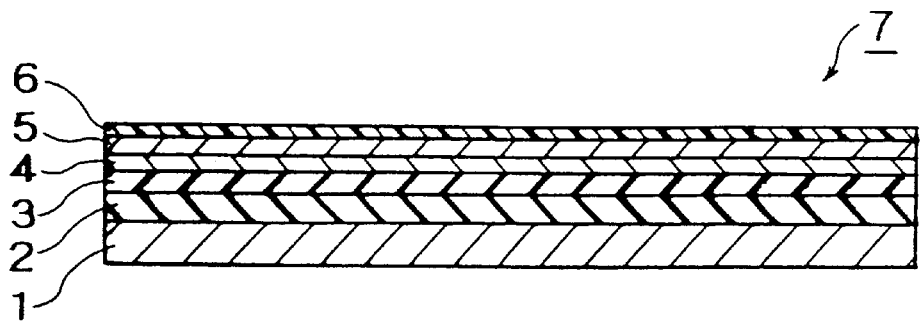
FIG. 9 is a partial cross-sectional view showing the structure of a magnetic recording medium produced in Example 3.

In the present Example, magnetic disks 7 having the structure as shown in FIG. 9 were produced using the compounds 1 to 37 as lubricants, and sliding performances of the lubricating films comprising the compounds were evaluated for each compound.

First, on the surface of an Al alloy disk 1 of 5.25 inches diameter, an Ni—P layer 2 and a Cr layer 3 were formed in this order in an superposes manner. Next, an Ni—Co type magnetic layer 4 (layer thickness: 50 nm) was formed on the surface of the Cr layer 3 by sputtering, and a 50 nm thick protective layer 5 consisting of carbon was further formed thereon.

Next, magnetic disks thus obtained were immersed for 1 minute in FC-72 solutions in which the compounds 1 to 37 stood dissolved respectively in a concentration of 0.1% by weight. Thereafter, these were drawn up at a rate of 1 mm/second, and were left for 2 hours at room temperature to volatilize the solvent. Thus, magnetic disks 7 were obtained on which lubricating films 6 comprising respectively the compounds 1 to 37 were formed as the outermost layers.

The sliding performance of the lubricating film 6 of each magnetic disk 7 was evaluated by frictional force at the time of stiction on the last cycle, which was measured by the CSS (contact start-stop) method using a CSS tester manufactured by Onoda Cement Co., Ltd. The results are shown in Table 3.

The measurement was made under conditions of number of revolution: 3,600 rpm; one cycle: 30 seconds; number of cycles in total: 1,000 cycles; and head load: 10 g.

As can be seen from Table 3, the compounds 1 to 37 all have a superior sliding performance. As can also be seen from these results, the compounds having the structure wherein oxyethylene moieties are bonded to the both terminals of a perfluoropolyoxyalkylene chain (the compounds 1 to 22) have a tendency to have a higher sliding performance than the compounds having the structure wherein an oxyethylene moiety is bonded to a terminal of a perfluoropolyoxyalkyl chain (the compounds 23 to 26, 30 to 34 and 37), and are more preferred.

TABLE 3

| Compound coated | 1 | 2 | 3 | 4 | 5 | 6 | 7 | 8 |
|---|---|---|---|---|---|---|---|---|
| CSS evaluation (g) | 7.7 | 7.3 | 7.9 | 7.8 | 7.9 | 7.7 | 8.2 | 7.5 |
| Compound coated | 9 | 10 | 11 | 12 | 13 | 14 | 15 | 16 |
| CSS evaluation (g) | 8.1 | 8.6 | 8.4 | 8.1 | 8.5 | 7.6 | 9.0 | 7.5 |
| Compound coated | 17 | 18 | 19 | 20 | 21 | 22 | 23 | 24 |
| CSS evaluation (g) | 7.7 | 8.2 | 8.7 | 8.9 | 9.5 | 11.5 | 10.2 | 13.2 |
| Compound coated | 25 | 26 | 27 | 28 | 29 | 30 | 31 | 32 |
| CSS evaluation (g) | 10.44 | 12.9 | 7.4 | 8.3 | 7.4 | 10.4 | 14.2 | 14.4 |
| Compound coated | 33 | 34 | 35 | 36 | 37 | | | |
| CSS evaluation (g) | 13.2 | 13.2 | 11.5 | 10.6 | 11.2 | | | |

EXAMPLE 4

Magnetic disk devices were assembled using the magnetic disks 7 produced in Example 3, and information was recorded and played backed. As a result, the devices worked normally also after 1,000-hour continuous drive.

Figure 10:
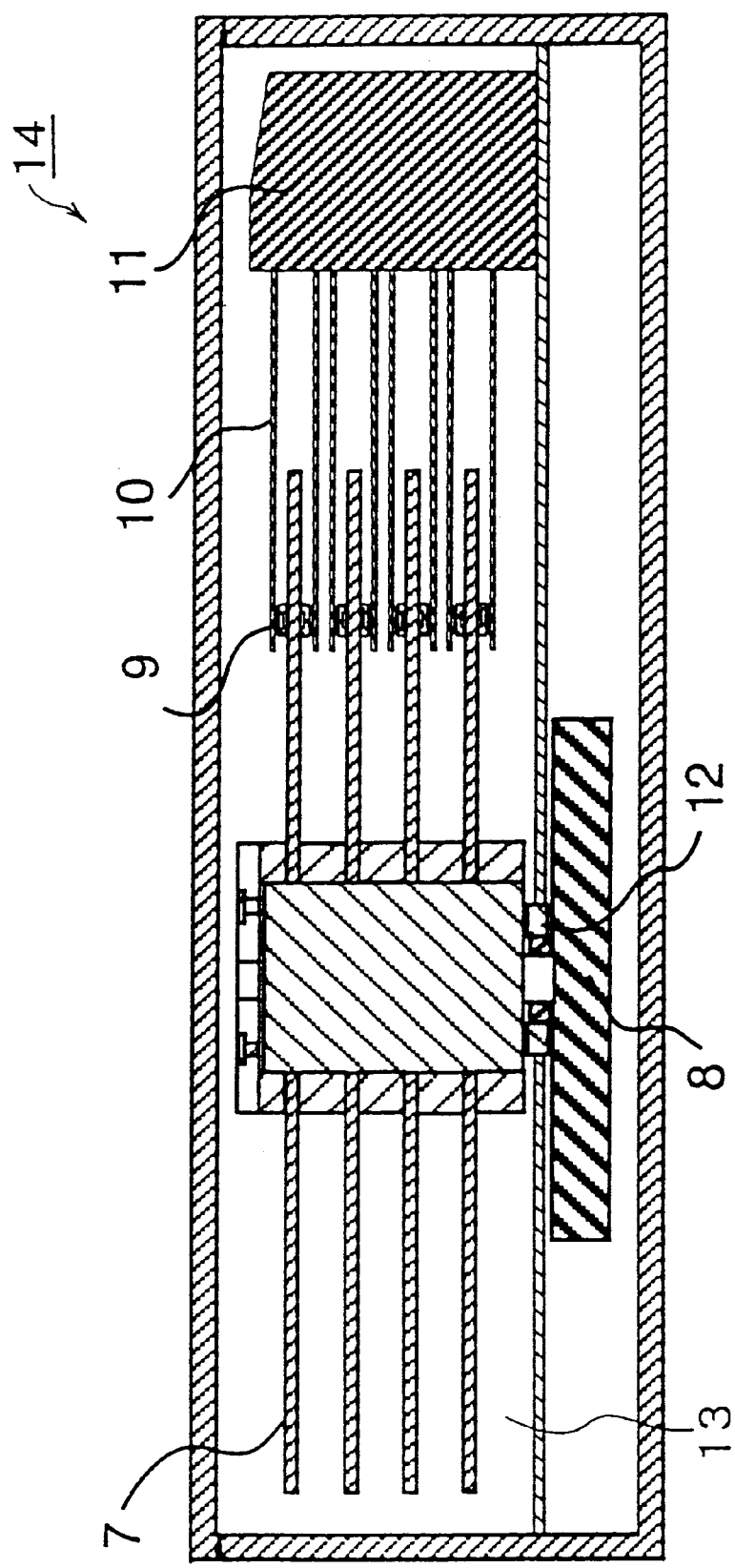
FIG. 10 is a partial cross-sectional view showing the structure of a magnetic disk device produced in Example 4.

As shown in FIG. 10, a magnetic disk device 14 of the present Example has a structure wherein four magnetic disks 7 are fixed to the rotating shaft portion of a rotation control mechanism, spindle motor 8, and each magnetic disk 7 is provided with a head slider 9 incorporated with recording-playbacking elements on its upper and lower sides. The head slider 9 is connected to a head slider positioning mechanism, actuator 11, via head suspensions 10. The magnetic disks 7, the head sliders 9, the head suspensions 10 and the actuator 11 are held in a hermetically sealed chamber 13 by mechanical sealing so that dust or the like can not enter from the outside.

COMPARATIVE EXAMPLE 2

A magnetic disk 7 was produced in the same manner as in Example 3 but using ammonium stearate, and the sliding performance of its lubricating film 6 was measured. As a result, its CSS evaluation had a value of 15 g or above. It is seen from this result that the compounds 1 to 37 all have a sliding performance superior to the conventional lubricant.

POSSIBILITY OF INDUSTRIAL APPLICATION

The fluorine-containing compound according to the present invention is useful as a surface modifier which can improve lubricity and water repellency of the surface to be treated, and is especially suited for use in lubricating films of magnetic recording media.

What is claimed is:

1. A fluorine-containing compound represented by the following general formula (1):

wherein $R^1$ is a perfluoropolyoxyalkylene chain having an average molecular weight of 800 or more, and $X^1$'s are each a group containing a cyclic polyether atomic group having at least 4 oxygen atoms, and also having an amide linkage, a sulfonamide linkage, an ether linkage or an ester linkage between $R^1$ and a remaining portion of $X^1$.

2. The compound according to claim 1, being represented by the following general formula (2):

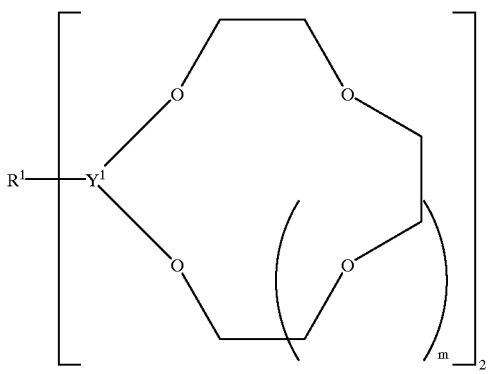

wherein $Y^1$ represents a trivalent group including an amide linkage, a sulfonamide linkage, an ether linkage or an ester linkage, and m represents an integer of 1 to 5.

3. A fluorine-containing compound represented by the following formula (3):

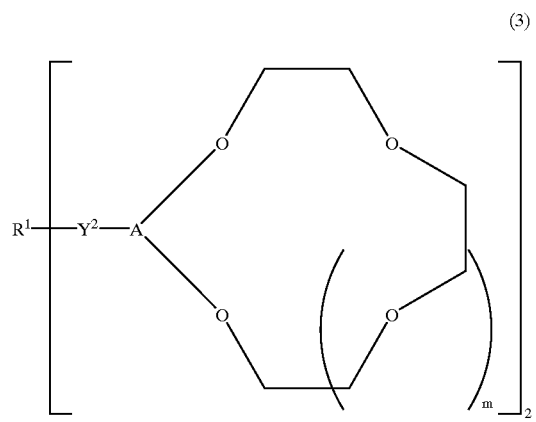

wherein A represents an aromatic ring; and $R^1$—$Y^2$— is $R^1$—CONH—, $R^1$—CH$_2$NRs—, $R^1$—CH$_2$OCH$_2$—, $R^1$—CO$_2$CH$_2$—, $R^1$—CH$_2$OCO—, $R^1$—CH$_2$OCOCH$_2$CH$_2$— or $R^1$—CH$_2$OCOCH=CH—, where Rs represents a toluenesulfonyl group, a methanesulfonyl group or a naphthalenesulfonyl group, and $R^1$ is a perfluoropolyoxyalkylene chain having an average molecular weight of 800 or more, and m represents an integer of 1 to 5.

4. A fluorine-containing compound represented by the following general formula (4):

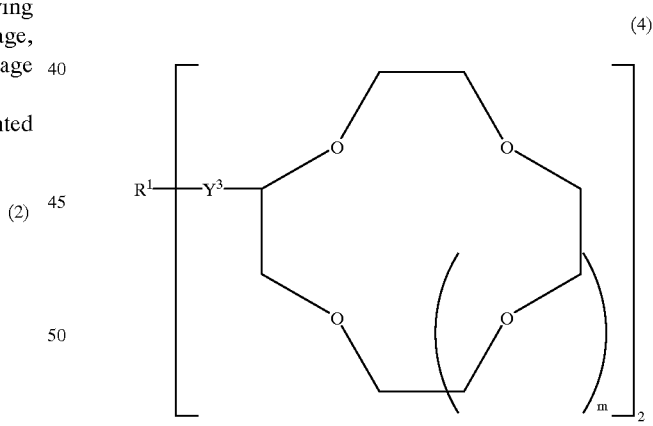

wherein $R^1$—$Y^3$— is $R^1$CONHCH$_2$—, $R^1$CH$_2$NRsCH$_2$—, $R^1$—CH$_2$OCH$_2$— or $R^1$—CO$_2$CH$_2$—, where Rs represents a toluenesulfonyl group, a methanesulfonyl group or a naphthalenesulfonyl group, and $R^1$ is a perfluoropolyoxyalkylene chain having an average molecular weight of 800 or more, and m represents an integer of 1 to 5.

5. The compound according to claim 2, being represented by the following general formula (5):

(5)

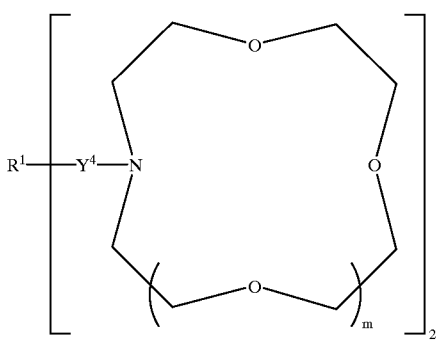

wherein $Y^4$ represents a divalent group including an amide linkage, a sulfonamide linkage, an ether linkage or an ester linkage, and m represents an integer of 1 to 5.

6. The compound according to claim 5, wherein the $Y^4$ is a carbonyl group.

7. A fluorine-containing compound represented by the following general formula (9):

(9)

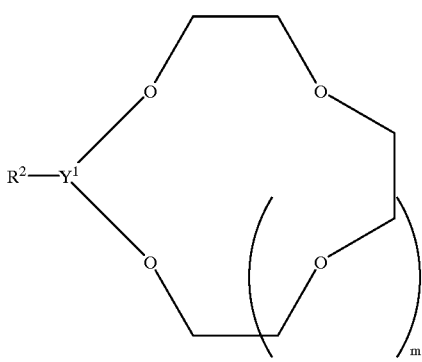

wherein $R^2$ is a perfluoropolyoxyalkyl chain having an average molecular weight of 800 or more, $Y^1$ represents a trivalent group including an amide linkage, a sulfonamide linkage, an ether linkage or an ester linkage, and m represents an integer of 1 to 5.

8. A fluorine-containing compound represented by the following general formula (10):

(10)

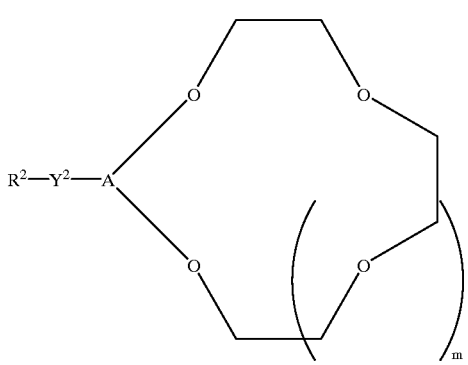

wherein A represents an aromatic ring; and $R^2$—$Y^2$— is $R^2$—CONH—, $R^2$—CH$_2$NRs—, $R^2$—CH$_2$OCH$_2$—, $R^2$—CO$_2$CH$_2$—, $R^2$—CH$_2$OCO—, $R^2$—CH$_2$OCOCH$_2$CH$_2$— or $R^2$—CH$_2$OCOCH=CH—, where Rs represents a toluenesulfonyl group, a methanesulfonyl group or a napthalenesulfonyl group, $R^2$ is a perfluoropolyoxyalkyl chain having an average molecular weight of 800 or more, and m represents an integer of 1 to 5.

9. A fluorine-containing compound represented by the following general formula (11):

(11)

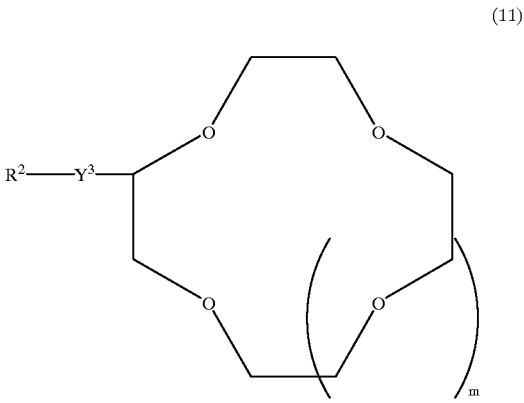

wherein $R^2$—$Y^3$— is $R^2$—CONHCH$_2$—, $R^2$—CH$_2$NRsCH$_2$—, $R^2$—CH$_2$OCH$_2$— or $R^2$—CO$_2$CH$_2$—, where Rs represents a toluenesulfonyl group, a methanesulfonyl group or a napthalenesulfonyl group, $R^2$ is a perfluoropolyoxyalkyl chain having an average molecular weight of 800 or more, an m represents an integer of 1 to 5.

10. The compound according to claim 7, being represented by the following general formula (12):

(12)

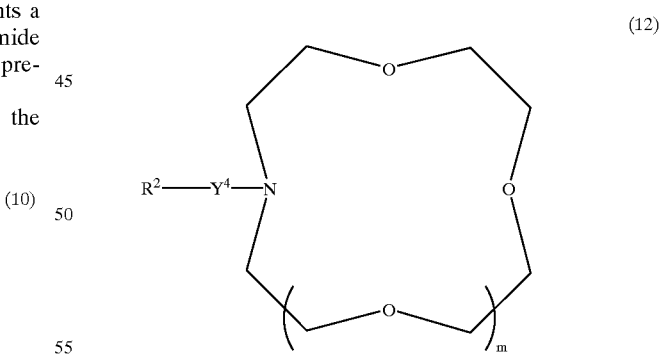

wherein $Y^4$ represents a divalent group including an amide linkage, a sulfonamide linkage, an ether linkage or an ester linkage.

11. The compound according to claim 10, wherein the $Y^4$ is a carbonyl group.

12. A fluorine-containing compound represented by the following general formula (13):

(13)

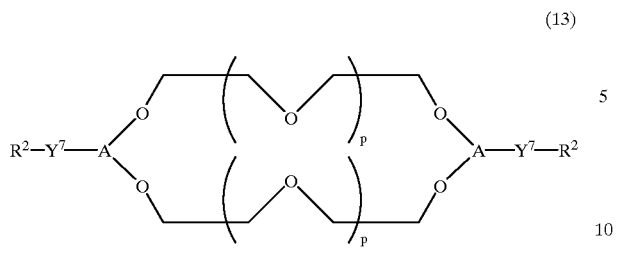

(16)

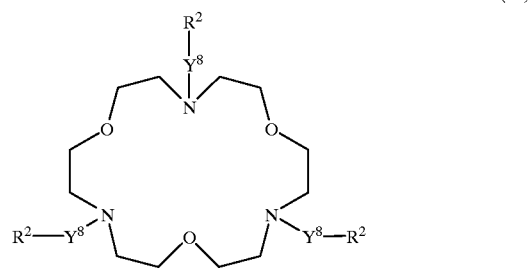

wherein $R^2$'s are each a perfluoropolyoxyalkyl chain having an average molecular weight of 800 or more; A's each represents an aromatic ring; $R^2$—$Y^7$—'s are each $R^2$—CONH—, $R^2$—$CH_2NRs$—, $R^2$—$CH_2OCH_2$—, $R^2$—$CO_2CH_2$—, $R^2$—$CH_2OCO$—, $R^2$—$CH_2OCOCH_2CH_2$— or $R^2$—$CH_2OCOCH$=CH—, where Rs represents a toluenesulfonyl group, a methanesulfonyl group or a napthalenesulfonyl group; and p represents an integer of 1 to 3.

13. A fluorine-containing compound represented by the following general formula (14):

16. The compound according to claim 13, wherein the $Y^8$'s are each a carbonyl group.

17. A lubricant comprising the fluorine-containing compound according to any one of claims 2, 5, 7, 10 and 13–15, and a base oil.

18. A surface modifier including a fluorine-containing compound, wherein said fluorine-containing compound is the fluorine-containing compound according to any one of claims 2, 5, 7, 10 and 13–15.

(14)

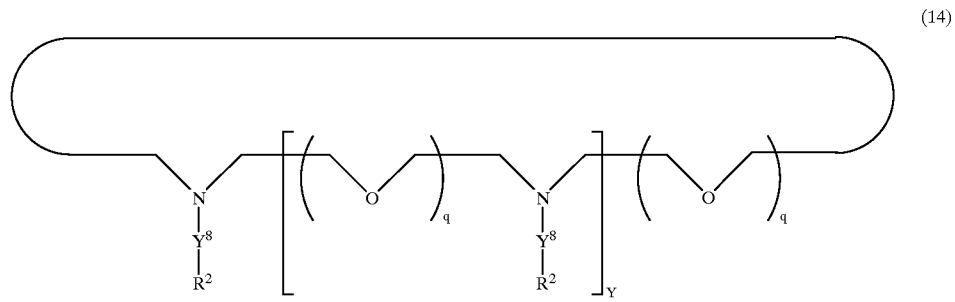

wherein $R^2$'s are each a perfluoropolyoxyalkyl chain having an average molecular weight of 800 or more, $Y^8$'s each represent a divalent group including an amide linkage, a sulfonamide linkage, an ether linkage or an ester linkage, q's are each an integer of 1 to 3, and r is an integer of 1 to 2.

14. The compound according to claim 13, being represented by the following general formula (15):

(15)

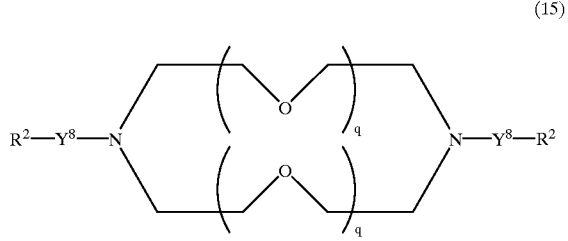

15. The compound according to claim 13, being represented by the following general formula (16):

19. A lubricating film comprising the fluorine-containing compound according to claim 1.

20. A magnetic recording medium having a non-magnetic support, at least one magnetic material layer provided on the non-magnetic support, and a lubricating film provided as an outermost layer, wherein said lubricating film comprises the fluorine-containing compound according to claim 1.

21. The magnetic recording medium according to claim 20, wherein said non-magnetic support comprises a glass containing sodium or potassium; and
said sodium and potassium in said glass being in a content of from 5% by weight to 20% by weight in sum total.

22. A magnetic recording device having the magnetic recording medium according to claim 21.

23. The magnetic recording device according to claim 22, wherein;
said magnetic recording medium is a magnetic disk; and
said device further has a magnetic head slider which performs at least one of the recording of information on the magnetic disk and the playbacking of information from the magnetic disk.

24. The magnetic disk device according to claim 23, wherein;

said magnetic disk comprises:

a non-magnetic support;

at least one magnetic material layer provided on the non-magnetic support; and a lubricating film provided as an outermost layer, said non-magnetic support comprising a glass containing sodium or potassium, said sodium and potassium in said glass being in a content of from 5% by weight of 20% by weight in sum total.

25. The magnetic disk device according to claim 23, wherein;

a shortest distance between said magnetic disk and said magnetic head slider at the time of recording and/or playbacking is 40 nm or less on average.

26. The magnetic disk device according to claim 23, wherein;

a coefficient of static friction between the surface of said magnetic disk and said magnetic head slider at the time of starting recording and/or playbacking is smaller than 1.00.

27. A magnetic disk device having a magnetic disk and a magnetic head slider which performed at least one of the recording of information on the magnetic disk and the playbacking of information from the magnetic disk, wherein:

said magnetic disk comprises at least a non-magnetic support, at least one magnetic material layer provided on the non-magnetic support, and a lubricating film provided as an outermost layer;

said lubricating film comprising a fluorine-containing compound represented by any one of the following general formulas (1), (9), (13), (14) and (17):

$$X^1—R^1—X^1 \tag{1}$$

wherein $R^1$ is a perfluoropolyoxyalkylene chain having an average molecular weight of 800 or more, and $X^1$'s are each a group containing a cyclic polyether atomic group having at least 4 oxygen atoms, and also having an amide linkage, a sulfonamide linkage, an ether linkage or an ester linkage between $R^1$ and a remaining portion of $X^1$;

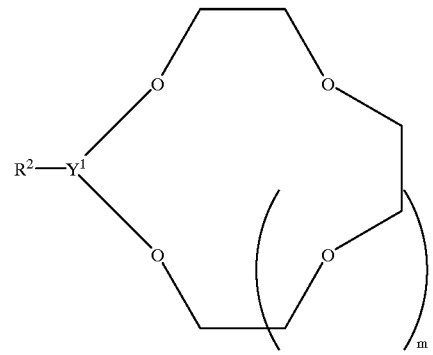

(9)

wherein $R^2$ is a perfluoropolyoxyalkyl chain having an average molecular weight of 800 or more, $Y^1$ represents a trivalent group including an amide linkage, a sulfonamide linkage, an ether linkage or an ester linkage, and m represents an integer of 1 to 5;

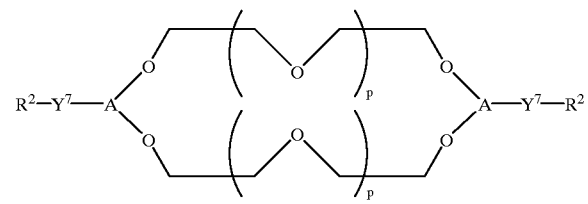

(13)

wherein $R^2$'s are each a perfluoropolyoxyalkyl chain having an average molecular weight of 800 or more; A's each represent an aromatic ring; $R^2$—$Y^7$—'s are each $R^2$—CONH—, $R^2$—CH$_2$NRs—, $R^2$—CH$_2$OCH$_2$—, $R^2$—CO$_2$CH$_2$—, $R^2$—CH$_2$OCO—, $R^2$—CH$_2$OCOCH$_2$CH$_2$— or $R^2$—CH$_2$OCOCH=CH—, where Rs represents a toluenesulfonyl group, a methanesulfonyl group or a napthalenesulfonyl group; and p represents an integer of 1 to 3;

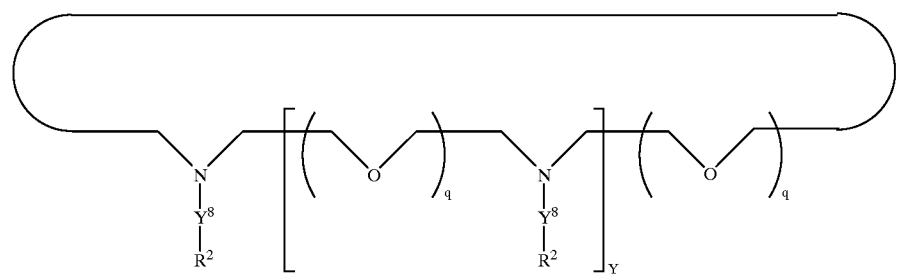

(14)

wherein $Y^2$'s are each a perfluoropolyoxyalkyl chain having an average molecular weight of 800 or more, $Y^8$'s each represent a divalent group including an amide linkage, a sulfonamide linkage, an ether linkage or an ester linkage, q's are each an integer of 1 to 3, and r is an integer of 1 or 2.

28. The magnetic disk device according to claim 27, wherein;

said magnetic disk comprises:

a non-magnetic support;

at least one magnetic material layer provided on the non-magnetic support; and a lubricating film provided as an outermost layer, said non-magnetic support comprising a glass containing sodium or potassium, said sodium and potassium in said glass being in a content of from 5% by weight to 20% by weight in sum total.

29. The magnetic disk device according to claim 27, wherein;

a shortest distance between said magnetic disk and said magnetic head slider at the time of recording and/or playbacking is 40 nm or less on average.

\* \* \* \* \*